United States Patent
Isozaki et al.

(10) Patent No.: US 12,311,115 B2
(45) Date of Patent: May 27, 2025

(54) VIBRATION CONTROL DEVICE, VIBRATION CONTROL METHOD, VIBRATION CONTROL PROGRAM, AND RECORDING MEDIUM

(71) Applicant: PIONEER CORPORATION, Tokyo (JP)

(72) Inventors: Kenta Isozaki, Kawagoe (JP); Takashi Morishige, Kawagoe (JP); Mitsuo Yasushi, Kawagoe (JP)

(73) Assignee: PIONEER CORPORATION, Tokyo (JP)

( * ) Notice: Subject to any disclaimer, the term of this patent is extended or adjusted under 35 U.S.C. 154(b) by 1026 days.

(21) Appl. No.: 17/282,688

(22) PCT Filed: Sep. 19, 2019

(86) PCT No.: PCT/JP2019/036711
§ 371 (c)(1),
(2) Date: Apr. 2, 2021

(87) PCT Pub. No.: WO2020/071136
PCT Pub. Date: Apr. 9, 2020

(65) Prior Publication Data
US 2021/0379328 A1 Dec. 9, 2021

(30) Foreign Application Priority Data
Oct. 3, 2018 (JP) .................. 2018-188004

(51) Int. Cl.
*A61M 21/02* (2006.01)
*A61M 21/00* (2006.01)
(Continued)

(52) U.S. Cl.
CPC ..... *A61M 21/02* (2013.01); *A61M 2021/0022* (2013.01); *A61M 2021/0027* (2013.01);
(Continued)

(58) Field of Classification Search
CPC ............................................ A61M 2021/0022
See application file for complete search history.

(56) References Cited

U.S. PATENT DOCUMENTS

| 2004/0097851 A1* | 5/2004 | Inada ................. A61H 23/0263 |
| | | 601/63 |
| 2017/0245070 A1 | 8/2017 | Inagaki et al. |
| 2018/0140798 A1* | 5/2018 | Tomiyama ............ A61M 21/02 |

FOREIGN PATENT DOCUMENTS

| CN | 108310586 A | * 7/2018 | ............. A61H 23/02 |
| JP | 2004-275668 | 10/2004 | |

(Continued)

OTHER PUBLICATIONS

International Search Report for PCT/JP2019/036711 dated Nov. 5, 2019, 5 pages.
(Continued)

*Primary Examiner* — Thaddeus B Cox
(74) *Attorney, Agent, or Firm* — NIXON & VANDERHYE

(57) ABSTRACT

A vibration control device that while responding to music being played, generates a vibration that gives desired arousal effect and/or relaxing effect regardless of the contents is provided, the vibration control device controlling a vibration device that generates vibration according to the music being played and gives a stimulus to a user includes a vibration signal acquisition unit for acquiring a vibration signal representing the vibration in which a stimulus intensity falls within a predetermined stimulus intensity range, and an output unit for outputting the vibration signal acquired by the vibration signal acquisition unit to the vibration device.

8 Claims, 9 Drawing Sheets

(51) Int. Cl.
  *B60N 2/90*   (2018.01)
  *H04R 5/02*   (2006.01)
(52) U.S. Cl.
  CPC .......... *B60N 2/90* (2018.02); *B60N 2002/981* (2018.02); *H04R 5/023* (2013.01); *H04R 2499/13* (2013.01)

(56) References Cited

FOREIGN PATENT DOCUMENTS

| | | |
|---|---|---|
| JP | 2013-251750 | 12/2013 |
| JP | 2014-126593 | 7/2014 |
| JP | 2015-045879 | 3/2015 |
| JP | 2008-000222 | 1/2018 |
| WO | 2016/027366 | 2/2016 |

OTHER PUBLICATIONS

Written Opinion of the ISA for PCT/JP2019/036711 dated Nov. 5, 2019, 5 pages.

* cited by examiner

| MUSIC/VIBRATION CORRESPONDENCE G DATA | | |
|---|---|---|
| MUSIC INFORMATION | SIGNAL SET | |
| MUSIC INFORMATION M1 | AROUSAL VIBRATION SIGNAL S11 | 232 |
| | NORMAL VIBRATION SIGNAL S12 | |
| | RELAX VIBRATION SIGNAL S13 | |
| MUSIC INFORMATION M2 | AROUSAL VIBRATION SIGNAL S21 | 232 |
| | NORMAL VIBRATION SIGNAL S22 | |
| | RELAX VIBRATION SIGNAL S23 | |
| ⋮ | ⋮ | |

| MAP DATA | | |
|---|---|---|
| LINK INFORMATION | STIMULUS INTENSITY INFORMATION | |
| | FREQUENCY RANGE | VIBRATION AMOUNT RANGE |
| GENERAL ROAD SECTION L11 | FOR DAYTIME A111 | FOR DAYTIME B111 |
| | FOR NIGHT A112 | FOR NIGHT B112 |
| HIGHWAY SECTION L12 | FOR DAYTIME A121 | FOR DAYTIME B121 |
| | FOR NIGHT A122 | FOR NIGHT B122 |
| START SECTION OF AUTONOMOUS DRIVING ROAD L13 | FOR DAYTIME A131 | FOR DAYTIME B131 |
| | FOR NIGHT A132 | FOR NIGHT B132 |
| END SECTION OF AUTONOMOUS DRIVING ROAD L14 | FOR DAYTIME A141 | FOR DAYTIME B141 |
| | FOR NIGHT A142 | FOR NIGHT B142 |
| ⋮ | ⋮ | ⋮ |

FIG.7

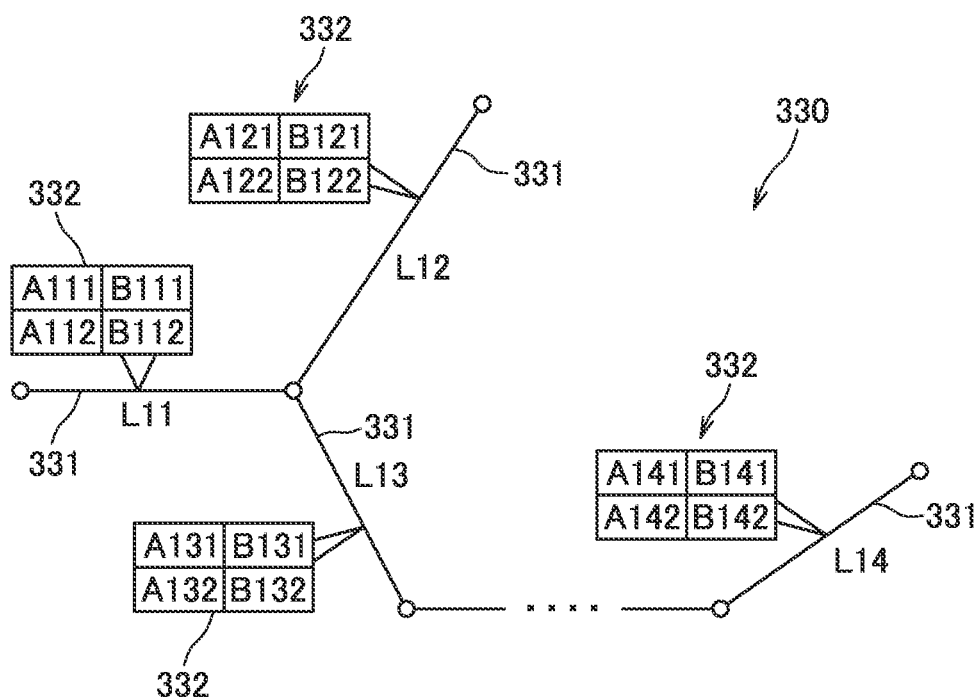

FIG.8

| MAP DATA | | | |
|---|---|---|---|
| MAP ELEMENT INFORMATION | STIMULUS INTENSITY INFORMATION | | |
| | FREQUENCY RANGE | VIBRATION AMOUNT RANGE | |
| FIRST ROAD LINK L21 | FOR DAYTIME A211 | FOR DAYTIME B211 | ⎫ 432 |
| | FOR NIGHT A212 | FOR NIGHT B212 | ⎭ |
| SECOND ROAD LINK L22 | FOR DAYTIME A221 | FOR DAYTIME B221 | ⎫ 432 |
| | FOR NIGHT A222 | FOR NIGHT B222 | ⎭ |
| FIRST NODE N23 | FOR DAYTIME A231 | FOR DAYTIME B231 | ⎫ 432 |
| | FOR NIGHT A232 | FOR NIGHT B232 | ⎭ |
| FIRST AREA Ar24 | FOR DAYTIME A241 | FOR DAYTIME B241 | ⎫ 432 |
| | FOR NIGHT A242 | FOR NIGHT B242 | ⎭ |
| ⋮ | ⋮ | ⋮ | |

FIG.10

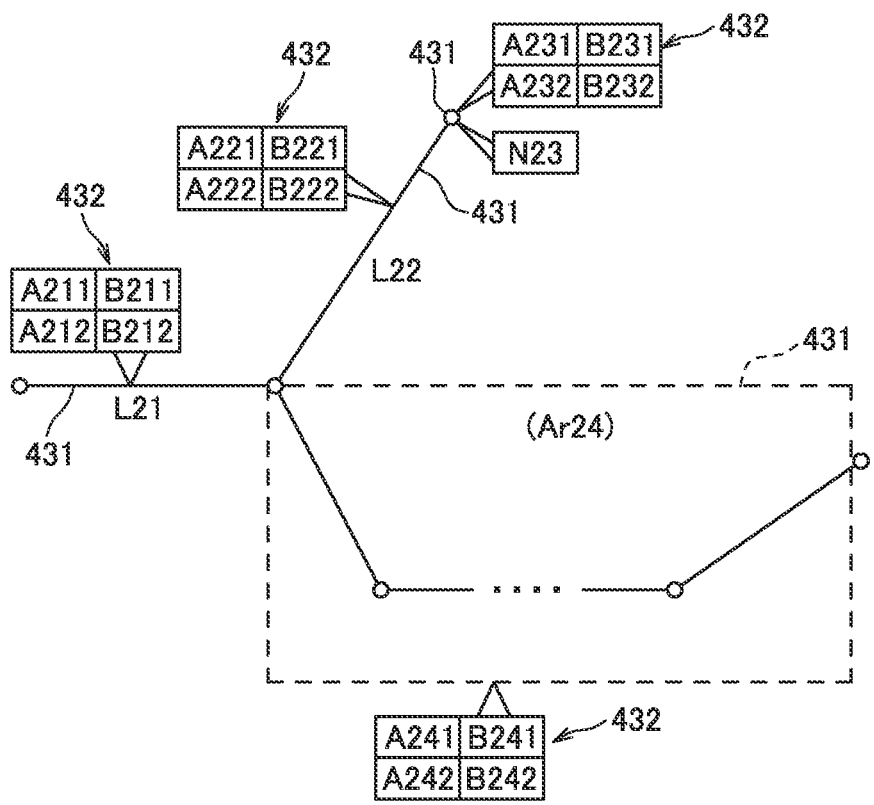

FIG.11

VIBRATION CONTROL DEVICE, VIBRATION CONTROL METHOD, VIBRATION CONTROL PROGRAM, AND RECORDING MEDIUM

CROSS-REFERENCE TO RELATED APPLICATIONS

This application is the U.S. national phase of International Application No. PCT/JP2019/036711 filed Sep. 19, 2019 which designated the U.S. and claims priority to JP 2018-188004 filed Oct. 3, 2018, the entire contents of each of which are hereby incorporated by reference.

BACKGROUND OF THE INVENTION

Field of the Invention

The present invention relates to a vibration control device for controlling a vibration device, a vibration control method, a vibration control program, and a storage medium.

Description of the Related Art

Conventionally, there is known a technique of vibrating a vibration device built in a moving body seat according to music being played by an audio device so as to cause a user to experience the music (see, for example, Patent Document 1). The technique described in Patent Literature 1 is configured to vibrate the vibration device with a signal obtained by amplifying a low frequency component of the music being played. Generating such vibration and giving the music a sense of experience can make entertainment enhanced. In addition, causing the user to experience the vibration as a stimulus can cause drowsy user to obtain an effect of arousal or, conversely, excited user to obtain an effect of relaxing.

CITATION LIST

Patent Literature

Japanese Patent Application Publication No. 2004-275668

SUMMARY OF THE INVENTION

However, since the above-mentioned technology generates vibration according to the music being played, it may be difficult to obtain an intended arousal effect and/or relaxing effect depending on the contents of the music.

Therefore, the subject of the present invention is to provide, for example, a vibration control device, a vibration control method, a vibration control program and a storage medium capable of generating vibration that can obtain a desired arousal effect and/or a relaxing effect regardless of the contents of the music while being played.

In order to solve the above-mentioned problems and achieve the object, the vibration control device of the present invention is a vibration control device that controls a vibration device that generates vibration according to the music being played and stimulate the user, which is provided with a vibration signal acquisition unit that acquires a vibration signal representing the vibration in which a stimulus intensity falls within a predetermined stimulus intensity range, and an output unit that outputs the vibration signal acquired by the vibration signal acquisition unit to the vibration device.

Further, in order to solve the above-mentioned problems and achieve the object, the vibration control method of the present invention is a vibration control method for controlling a vibration device that generates vibration according to the music being played and stimulate the user, which is provided with a vibration signal acquisition step of acquiring a vibration signal representing the vibration in which the stimulus intensity falls within a predetermined stimulus intensity range, and an output step of outputting the vibration signal acquired in the vibration signal acquisition step to the vibration device.

Further, in order to solve the above-mentioned problems and achieve the object, the vibration control program of the present invention is to cause a computer to execute the above-mentioned vibration control method of the present invention.

Further, in order to solve the above-mentioned problems and achieve the object, the storage medium of the present invention is to store the above-mentioned vibration control program of the present invention.

BRIEF DESCRIPTION OF THE DRAWINGS

FIG. 4 is a schematic diagram showing in a table format a data structure of a music/vibration correspondence data shown in FIG. 3;

FIG. 7 is a schematic diagram showing in a table format a data structure of a map data shown in FIG. 6;

FIG. 8 is a schematic diagram showing in a map format a data structure shown in a table format in FIG. 7;

FIG. 10 is a schematic diagram showing in a table format a data structure of a modification example with respect to the data structure of the map data shown in FIGS. 7 and 8; and FIG. 11 is a schematic diagram showing in a map format a data structure shown in a table format in FIG. 10.

DETAILED DESCRIPTION OF THE PREFERRED EMBODIMENTS

Figure 1:
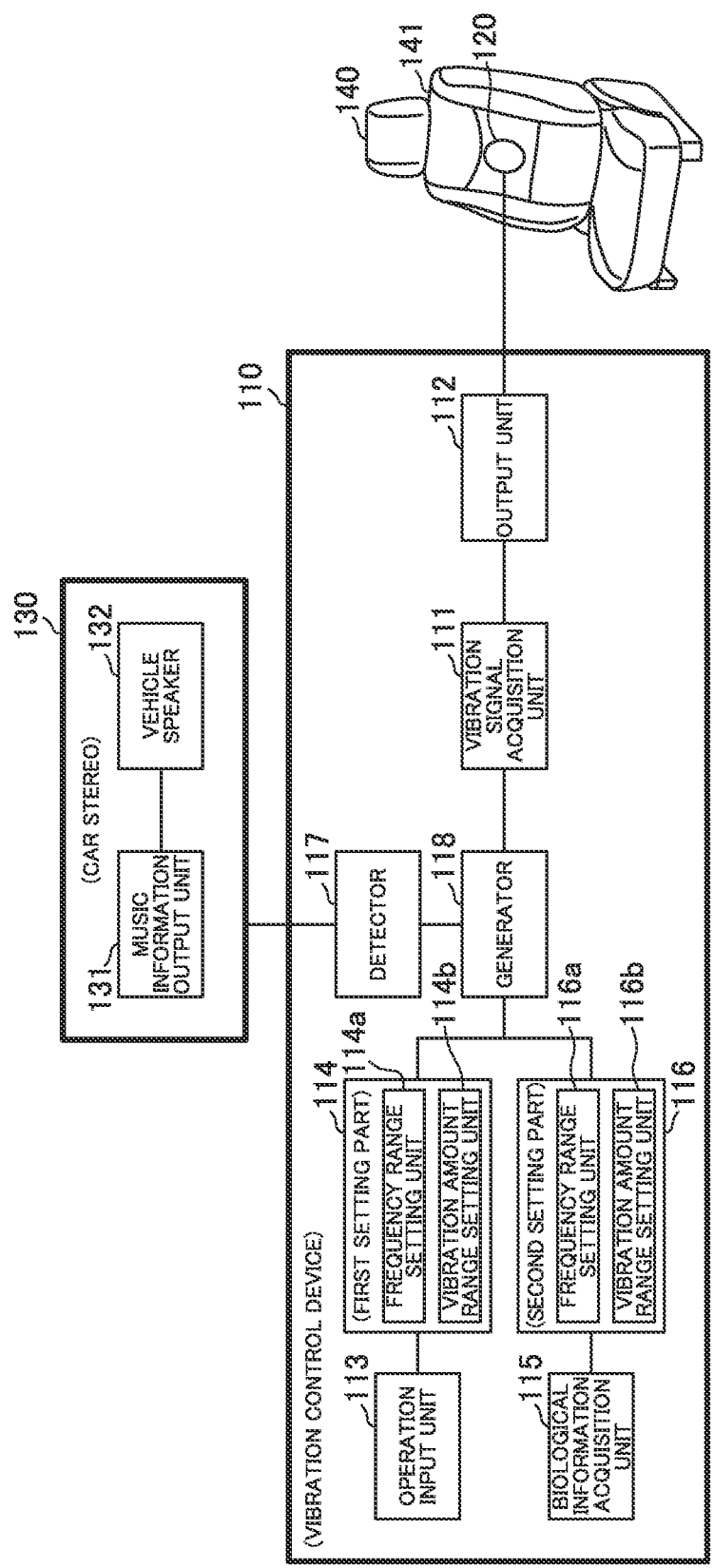
FIG. 1 is a schematic block diagram showing a vibration control device mounted on a moving body according to a first embodiment.

Hereinafter, embodiments of the present invention will be described. The vibration control device according to the embodiment of the present invention is a vibration control device for controlling a vibration device that generates vibration according to music being played and stimulating the user, and including a vibration signal acquisition unit and an output unit. The vibration signal acquisition unit acquires a vibration signal representing vibration in which the stimulus intensity falls within a predetermined stimulus intensity range. The output unit outputs the vibration signal acquired by the vibration signal acquisition unit to the vibration device.

According to the vibration control device of the present embodiment, the vibration signal representing vibration within a predetermined stimulus intensity range is acquired and output to the vibration device while responding to the music being played. Therefore, such an effect can be obtained regardless of the contents of the music being played by performing an operation such as setting the stimulus intensity range to a desired range in which a desired arousal effect and/or a relaxing effect can be obtained. As described above, according to the vibration control device of the present embodiment, the vibration can be generated that can obtain the desired arousal effect and/or the relaxing effect regardless of the contents of the music while responding to the music being played.

Here, in the present embodiment, the vibration signal acquisition unit acquires as a vibration signal a signal representing the vibration whose vibration frequency falls within a predetermined frequency range.

When the user is allowed to experience the vibration as a stimulus, a frequency range of 20 Hz to 200 Hz can be mentioned as an example of a frequency range suitable for producing an arousal effect and/or a relaxing effect. According to the present embodiment, the vibration frequency of the vibration represented by the vibration signal acquired by the vibration signal acquisition unit is limited to such a frequency range to generate vibration in which the arousal effect and/or the relaxing effect can be appropriately obtained.

Further, in the present embodiment, the vibration signal acquisition unit acquires as the vibration signal a signal representing vibration corresponding to at least one of the tempo of the music and the frequency of a sound constituting the code included in the music.

According to the present embodiment, the vibration of the vibration signal acquired by the vibration signal acquisition unit corresponds to the tempo of the music being played and the frequency of the sound constituting the code, so that the vibration generated by the vibration device does not impair the taste of the music being played. As described above, according to the present embodiment, the vibration for obtaining the arousal effect and/or the relaxing effect can be generated without impairing the taste of the music being played.

Further, in the present embodiment, the vibration signal acquisition unit acquires as the vibration signal a signal representing the vibration corresponding to the tempo of music in which an occurrence frequency of the vibration falls within a predetermined occurrence frequency range as the stimulus intensity range.

The occurrence frequency of vibration, which is determined according to the tempo of the music being played, can be used as an index indicating the stimulus intensity given by the vibration. According to the present embodiment, the occurrence frequency is adopted as such an index, and the stimulus intensity range is specifically set as the occurrence frequency range, so that the vibration that obtains the desired arousal effect and/or relaxing effect can be effectively generated.

Further, in the present embodiment, the vibration signal acquisition unit acquires as the vibration signal a signal representing vibration corresponding to the frequency of the sound constituting the music code.

According to the present embodiment, generating vibration according to the frequency of the sound constituting the music code can cause the vibration to generate for obtaining the arousal effect and/or the relaxing effect without impairing the taste of the music being played.

Further, in the present embodiment, the vibration signal acquisition unit acquires as the vibration signal a signal representing vibration in which the vibration amount of the vibration falls within a predetermined vibration amount range as the stimulus intensity range.

The vibration amount can be adopted as an index showing the stimulus intensity given by the vibration. According to the present embodiment, the vibration amount is adopted as such an index, and the stimulus intensity range is specifically set as the vibration amount range, so that the vibration can be generated effectively that obtains the desired arousal effect and/or the relaxing effect.

Further, the vibration control device of the present embodiment includes a first setting unit that sets a stimulus intensity range in response to a user operation. Then, the vibration signal acquisition unit acquires a signal representing vibration whose stimulus intensity falls within the stimulus intensity range set by the first setting unit as the vibration signal.

According to the present embodiment, the user can adjust the stimulus intensity range, that is, the stimulus intensity given by the vibration to his/her desired intensity through the first setting unit. This makes it possible to effectively generate the vibration that provides the desired arousal and/or relaxing effect.

Further, the vibration control device of the present embodiment includes a biological information acquisition unit and a second setting unit. The biological information acquisition unit acquires biological information representing the biological state of the user. The second setting unit sets the stimulus intensity range based on the biological information acquired by the biological information acquisition unit. Then, the vibration signal acquisition unit acquires a signal representing vibration whose stimulus intensity falls within the stimulus intensity range set by the second setting unit as the vibration signal.

According to the present embodiment, since an appropriate stimulus according to the biological condition is given to the user, it is possible to generate the vibration that appropriately obtains the desired arousal effect and/or the relaxing effect.

Further, the vibration control device of the present embodiment includes a detection unit and a generation unit. The detection unit detects from the music as a music element at least one of a tempo of the music and a frequency of the sound constituting code included in the music. The generation unit generates the vibration signal based on the music element detected by the detection unit. Then, the vibration signal acquisition unit acquires the vibration signal generated by the generation unit.

According to the present embodiment, generating the vibration signal based on the music element detected from the music being played can make the vibration for obtaining the arousal effect and/or the relaxing effect generated without further impairing the taste of the music being played.

Further, the vibration control method according to the embodiment of the present invention is a vibration control method for controlling a vibration device that generates a vibration corresponding to music being played to give stimulation to a user, and includes a vibration signal acquisition step and an output step. The vibration signal acquisition step is a step of acquiring a vibration signal representing vibration in which the stimulus intensity falls within a predetermined stimulus intensity range. The output step is a step of outputting the vibration signal acquired in the vibration signal acquisition step to the vibration device.

According to the vibration control method of the present embodiment, the vibration signal representing vibration within the predetermined stimulus intensity range is acquired and output to the vibration device while responding to the music being played. Therefore, vibration can be generated in the vibration device through which such an effect can be obtained regardless of the contents of the music being played by performing an operation such as setting the stimulus intensity range to the desired range in which the desired arousal effect and/or the relaxing effect can be obtained. As described above, according to the vibration control method of the present embodiment, it is possible to generate the vibration that can obtain the desired arousal effect and/or the relaxing effect regardless of the contents of the music while responding to the music being played.

Further, the vibration control program according to the embodiment of the present invention is a program that causes a computer to execute the above-mentioned vibration control method.

According to the vibration control program of the present embodiment, causing the computer to execute the above-mentioned vibration control method can generate the vibration in which the desired arousal effect and/or relaxing effect can be obtained regardless of the contents of the music being played.

Further, the storage medium according to the embodiment of the present invention stores the above-mentioned vibration control program.

According to the storage medium of the present embodiment, causing the computer to execute the above-mentioned vibration control method via the stored vibration control program can generate the vibration in which the desired arousal effect and the desired arousal effect and/or the relaxing effect can be obtained regardless of the contents of the music being played.

Embodiments

Hereinafter, an embodiment for solving the problem of generating vibration that can obtain a desired arousal effect and/or relaxing effect regardless of the contents while responding to music being played is specifically described with reference to the figures. First, a first embodiment will be described.

FIG. 1 is a schematic block diagram showing a vibration control device according to the first embodiment mounted on a moving body.

In this embodiment, the moving body is a passenger car, on which a vibration control device 110, a vibration device 120, and a car stereo 130 are mounted.

The car stereo 130 reproduces the music inside the moving body, and includes a music information output unit 131 and a vehicle speaker 132. The music information output unit 131 outputs music information acquired from a medium such as a CD (compact disc) or from a network via wireless communication to the vehicle speaker 132. The vehicle speaker 132 generates the music represented by the music information. At this time, in this embodiment, the music information output unit 131 also outputs the music information representing the music being played to the vibration control device 110. At this time, the music information output to the vibration control device 110 may be digital information such as MIDI (Musical Instrument Digital Interface), I2S (Inter-IC Sound), or analog information.

The vibration device 120 is a device that is embedded in a back plate 141 of the moving body seat 140 and generates the vibration according to the music being played to stimulate the user. The vibration device 120 receives a vibration signal representing vibration from the vibration control device 110, and generates vibration represented by the vibration signal. The power of the vibration device 120 is basically turned on at the same time as music playback on the car stereo 130, and is turned off when the music is completed to playback on the car stereo 130. Further, when on/off instructions are given by the user via an operation input unit 113 described later during music playback, the power is turned on/off according to the instructions.

The vibration control device 110 outputs the above vibration signal to control the vibration device 120, and is built on some computer mounted on the moving body. The vibration control device 110 includes a vibration signal acquisition unit 111, an output unit 112, an operation input unit 113, a first setting unit 114, a biological information acquisition unit 115, a second setting unit 116, a detection unit 117, and a generation unit 118.

The vibration signal acquisition unit 111 acquires a vibration signal representing vibration in which the intensity of the generated stimulus falls within a predetermined stimulus intensity range. In this embodiment, the vibration signal is internally generated in the vibration control device 110, and the vibration signal acquisition unit 111 acquires the internally generated vibration signal.

The output unit 112 outputs the vibration signal acquired by the vibration signal acquisition unit 111 to the vibration device 120.

The operation input unit 113 receives an operation from the user regarding on/off of the vibration device 120 and increase/decrease in the intensity of the vibration stimulus generated by the vibration device 120. When the vibration device 120 is instructed to be turned off at the operation input unit 113, the output unit 112 stops an output of the vibration signal to the vibration device 120 and turns off the power supply of the vibration device 120. Further, when the vibration device 120 is instructed to be turned on at the operation input unit 113 after the power supply is temporarily cut off during music playback, the output unit 112 turns on the power supply of the vibration device 120 to resume outputting the vibration signal.

The first setting unit 114 sets the stimulus intensity range according to the increase/decrease operation received at the operation input unit 113. Here, the vibration signal acquisition unit 111 acquires the vibration signal representing an intermittent vibration according to the tempo of the music being played. Then, in this embodiment, the occurrence frequency, which is the number of occurrences of vibration per unit time, and the vibration amount corresponding to the amplitude of vibration are adopted as indicators of the intensity of stimulation. Therefore, the first setting unit 114 includes an occurrence frequency range setting unit 114a for setting the occurrence frequency range as the stimulus intensity range, and a vibration amount range setting unit 114b for setting the vibration amount range as the stimulus intensity range.

The occurrence frequency range setting unit 114a in the first setting unit 114 sets the occurrence frequency range by shifting and adjusting the occurrence frequency range according to the increase/decrease operation received at the operation input unit 113. Further, the vibration amount range setting unit 114b in the first setting unit 114 sets the vibration amount range by shifting and adjusting the vibration amount range according to the increase/decrease operation received at the operation input unit 113.

The biological information acquisition unit 115 acquires biological information representing the biological state of the user. Specifically, the biological information acquisition unit 115 monitors a heart rate, a brain wave, a respiratory rate, an eye movement, a blinking, a line-of-sight direction, etc. of the user by using various sensors installed inside the moving body. Then, the user detects and acquires which of drowsiness-causing drowsy state, a normal arousal state, and an excited state is in a biological state. The arousal state referred to here corresponds to a sedative state with respect to an excited state.

The second setting unit 116 sets the occurrence frequency range and the vibration amount range as the stimulus intensity range based on the biological state acquired by the biological information acquisition unit 115, and includes the occurrence frequency range setting unit 116a and the vibration amount range setting unit 116b.

The occurrence frequency range setting unit 116a in the second setting unit 116 sets the occurrence frequency range according to the acquired biological information. When the biological information is in drowsy, the occurrence frequency range is set to the arousal occurrence frequency range corresponding to a large occurrence frequency in which a strong stimulus is given to promote arousal. When the biological information is in arousal, the occurrence frequency range is set to the normal occurrence frequency range corresponding to a normal occurrence frequency in which a moderate stimulus is given. Further, when the biological information is in the excited state, the occurrence frequency range is set to a relaxation occurrence frequency range corresponding to a small occurrence frequency in which a weak stimulus is given for relaxation.

The vibration amount range setting unit 116b in the second setting unit 116 sets the vibration amount range according to the acquired biological information. When the biological information is in a drowsy state, the vibration amount range is set to the arousal vibration amount range corresponding to a large vibration amount that gives a strong stimulus to promote arousal. When the biological information is in the arousal state, the vibration amount range is set to the normal vibration amount range corresponding to the normal vibration amount that gives a moderate stimulus. When the biological information is in an excited state, the vibration amount range is set to a relaxation vibration amount range corresponding to a small vibration amount in which a weak stimulus is given to relax.

Based on the music information sent from the music information output unit 131 of the car stereo 130, the detection unit 117 detects from the music being played three musical elements of the tempo of the music, the frequency of the sound constituting the code of the music, and the strength of the sound in the music. The tempo is detected with a known BPM (Beats Per Minute) detection technique. The frequency of the sound constituting the code is detected with a known code analysis technique. The strength of the sound is obtained directly from the music information.

The generation unit 118 generates the vibration signal based on three musical elements of the tempo, the frequency of the sound constituting the code, and the strength of the sound, detected by the detection unit 117.

First, the generation unit sets the occurrence frequency of the vibration represented by the vibration signal based on the tempo, and sets the frequency of vibration based on the frequency of the sounds that make up the code. The occurrence frequency is set to the same as the tempo, or an integral multiple thereof, or 1/integer. The vibration amount is set based on the strength of the sound represented by the music information.

The generator basically sets the frequency to the same frequency as the frequency of the sounds that make up the code. At this time, the frequency is adjusted so that the set frequency falls within the predetermined occurrence frequency range. As this occurrence frequency range, in this embodiment, a frequency range of 20 Hz to 200 Hz is set as an example of a frequency range suitable for providing the arousal effect and/or the relaxing effect. If the frequency set based on the code does not fall within this frequency range, the frequency is adjusted so as to fall within this frequency range by changing octave or the like. In addition, this adjustment may be performed by frequency conversion using a LUT (Lookup Table) for conversion.

Here, in this embodiment, the generation unit 118 adjusts the occurrence frequency once set as described above so as to fall within the occurrence frequency range set based on the biological information in the second setting unit 116. When the occurrence frequency range is adjusted by receiving the user operation at the first setting unit 114, the occurrence frequency is adjusted to increase or decrease so as to fall within the adjusted occurrence frequency range.

Further, the generation unit 118 adjusts the vibration amount once set as described above so as to be within the vibration amount range set based on the biological information in the second setting unit 116. When the vibration amount range is adjusted by the user operation in the first setting unit 114, the vibration amount is increased or decreased so as to be within the adjusted vibration amount range.

Here, the generation unit 118 generates the vibration signal based on the tempo of the music being played, the frequency of the sound constituting the code, and the strength of the sound. In addition, thereto, the following vibration signal arranged based on a music element may be generated. Musical elements for arrangement include timbre, length of one sound, fluctuation of sound pressure level, speed of sound rise (feeling of attack), and the like.

The vibration signal acquisition unit 111 acquires the vibration signal thus generated by the generation unit 118, and the output unit 112 outputs the acquired vibration signal to the vibration device 120.

Figure 2:
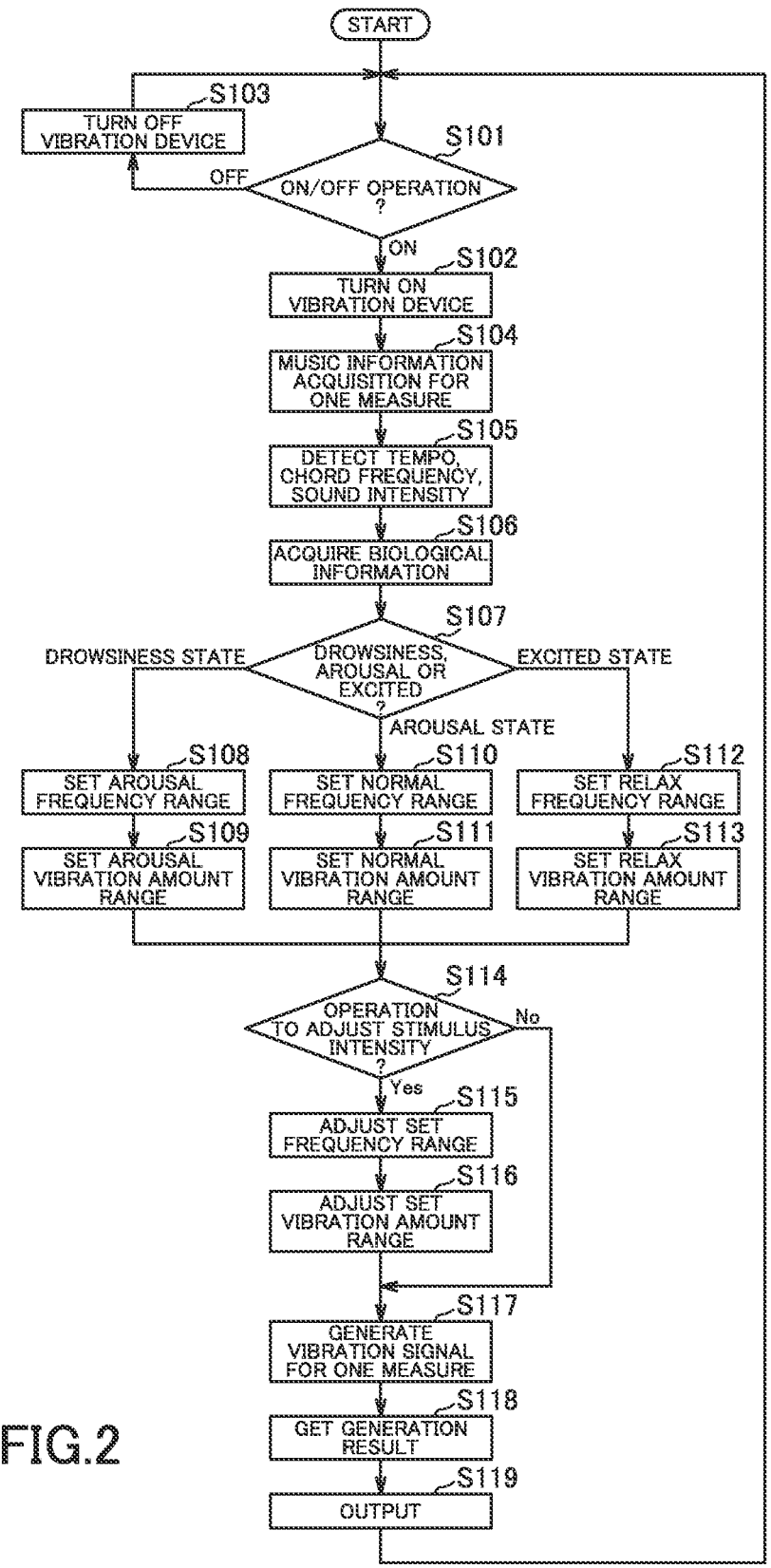
FIG. 2 is a flowchart showing a processing flow of a vibration control method executed by the vibration control device shown in FIG. 1.

FIG. 2 is a flowchart showing a processing flow of a vibration control method executed by the vibration control device shown in FIG. 1.

The process represented by this flowchart starts when the car stereo 130 starts playing music and the music information is sent to the vibration control device 110.

When the process starts, the generation unit 118 first determines whether or not the operation input unit 113 has been turned on/off for the power supply of the vibration device 120 after the music playback has started (step S101). When no particular operation is performed or when an on-operation is performed (on-determination in step S101), the output unit 112 turns on if the vibration device 120 is powered off at this time (step S102). In step S102, if the vibration device 120 is powered on at this time, no particular process is performed and the process proceeds to the next step S104.

On the other hand, when the off-operation is performed (off-determination in step S101), the output unit 112 turns off if the vibration device 120 is powered on at this time (step S103), and returns to the process of step S101. In step S103, if the vibration device 120 is powered off at this time, no particular process is performed and the process returns to step S101.

When the process proceeds to step S104 through step S102, the detection unit 117 in this step S104 acquires the music information for one measure of the music being played from the music information output unit 131 of the car stereo 130. Subsequently, the detection unit 117 detects the tempo, the frequency of the sound constituting the code, and the strength of the sound based on the acquired music information (step S105).

Further, the biological information acquisition unit 115 acquires the biological information representing whether the user's biological state is the drowsy state, the normal arousal state, or the excited state (step S106).

Next, the second setting unit 116 determines whether the biological state represented by the acquired biological information is the drowsy state, the arousal state, or the excited state (step S107).

When the biological state is drowsy state (drowsiness determination in step S107), the occurrence frequency range setting unit 116a of the second setting unit 116 sets the occurrence frequency range to the arousal occurrence frequency range (step S108). Further, the vibration amount range setting unit 116b sets the vibration amount range to the arousal vibration amount range (step S109).

When the biological state is the arousal state (arousal determination in step S107), the occurrence frequency range setting unit 116a of the second setting unit 116 sets the occurrence frequency range to the normal occurrence frequency range (step S110). Further, the vibration amount range setting unit 116b sets the vibration amount range to the normal vibration amount range (step S111).

When the biological state is the excited state (excitement determination in step S107), the occurrence frequency range setting unit 116a of the second setting unit 116 sets the occurrence frequency range to the relax occurrence frequency range (step S112). Further, the vibration amount range setting unit 116b sets the vibration amount range to the relax vibration amount range (step S113).

When the occurrence frequency range and the vibration amount range are set in this way, the generation unit 118 next determines whether or not the stimulus intensity adjustment operation has been performed on the operation input unit 113 after the music starts to playback (step S114).

When an adjustment is operated (yes determination in step S114), the occurrence frequency range setting unit 114a of the first setting unit 114 adjusts the set occurrence frequency range in increase/decrease according to the operation amount (step S115). Further, the vibration amount range setting unit 114b adjusts the set vibration amount range in increase/decrease according to the operation amount (step S116).

If no adjustment is operated (No determination in step S114), step S115 and step S116 are omitted, and the process proceeds to the next step S117.

In step S117, the generation unit 118 generates the corresponding vibration signal corresponding to the music information of one measure based on the tempo, the frequency of the sound constituting the code, the strength and weakness of the sound, the occurrence frequency range, and the vibration amount range obtained by the processing up to this point. That is, the occurrence frequency falls within the occurrence frequency range according to the tempo of the one measure, the frequency falls within the frequency range of 20 Hz to 200 Hz while corresponding to the code of the one measure and the vibration amount generates the vibration signal representing vibration within the vibration amount range while corresponding to the strength of the sound of the one measure.

The vibration signal acquisition unit 111 acquires the vibration signal for one measure thus generated (step S118), and the output unit 112 outputs the vibration signal to the vibration device 120 (step S119). After that, the process returns to step S101 and the subsequent processes are repeated. In the embodiment, the music information of the music being played is acquired in units of one measure, and the corresponding vibration signal is generated in units of one measure. However, the processing breaks are not limited to units of one measure and the processing may be performed in any unit. For example, music information for a unit time may be acquired and a corresponding vibration signal may be generated at a unit time interval.

The processing of this flowchart is continued until the music is completed to playback on the car stereo 130.

In this embodiment, the vibration control program for executing the vibration control method shown in the flowchart in FIG. 2 via the computer is stored in a storage medium of some computer mounted on the moving body. Further, the storage medium for storing this vibration control program is not limited to the storage medium of some computer mounted on the mobile body, but may be a known portable storage medium or a storage medium installed in a server connected to this computer via a network.

According to the vibration control device 110, the vibration control method, the vibration control program, and the storage medium of the first embodiment described above, the following effects can be obtained.

According to this embodiment, the vibration signal representing the vibration in which the stimulus intensity falls within the predetermined stimulus intensity range is acquired and output to the vibration device 120 while responding to the music being played. Therefore, the operation such as setting the stimulus intensity range to the desired range in which the desired arousal effect and/or the relaxing effect can be obtained, and such an effect can thus be generated in the vibration device 120 regardless of the contents of the music being played. As described above, according to the vibration control device 110 of the present embodiment, it is possible to generate the vibration that can cause the desired arousal effect and/or the relaxing effect regardless of the contents of the music while responding to the music being played.

In this embodiment, the vibration device 120 and the vibration control device 110 mounted on the moving body are exemplified, but the installation location of the vibration device 120 and the vibration control device 110 is not limited to the moving body. The vibration device 120 and the vibration control device 110 may be installed on a seat placed in a movie theater or a general residence as long as the user can be stimulated by vibration, and the installation location can be set arbitrarily.

Further, the installation position of the vibration device 120, even when mounted on the moving body, is not limited to the back plate 141 of the seat 140 as in the present embodiment, and can be set arbitrarily as long as the user can get stimulation.

Here, in this embodiment, the vibration signal acquisition unit 111 acquires the signal representing vibration whose vibration frequency falls within the frequency range of 20 Hz to 200 Hz as the vibration signal.

When the user is allowed to experience vibration as the stimulus, the above frequency range of 20 Hz to 200 Hz can be mentioned as an example of the frequency range suitable for producing the arousal effect and/or the relaxing effect. This is because vibration having a frequency lower than 20 Hz resonate with human internal organs, and vibrations having a frequency higher than 200 Hz cause humans to feel awkward, and each of them becomes relatively uncomfortable. According to this embodiment, the vibration frequency of the vibration represented by the vibration signal acquired by the vibration signal acquisition unit 111 is suppressed to such frequency range, and vibration can be generated in which the arousal effect and/or the relaxing effect can be appropriately obtained.

The frequency range for containing the vibration frequency is not limited to the range of 20 Hz to 200 Hz, and can be appropriately set as long as suitable for producing an arousal effect and/or a relaxing effect.

Further, in this embodiment, the vibration signal acquisition unit 111 acquires as the vibration signal the signal representing vibration according to the tempo of the music, the frequency of the sound constituting the code included in the music, and the strength of the sound.

According to this embodiment, as the vibration of the vibration signal acquired by the vibration signal acquisition unit 111 corresponds to the tempo of the music being played, the frequency of the sound constituting the code, and the strength of the sound, the vibration generated by the vibration device 120 does not easily impair the taste of the music being played. As described above, according to the present embodiment, the vibration for obtaining the arousal effect and/or the relaxing effect can be generated without impairing the taste of the music being played.

The vibration represented by the vibration signal may be based only on the tempo or only the frequency of the sound constituting the code, as long as the vibration corresponds to at least one of the tempo and the frequency of the sound constituting the code. In this case, the vibration element determined by the elements other than the tempo and the vibration element determined by the elements other than the frequency of the sound constituting the code are set according to some setting rule.

Further, in the present embodiment, the vibration signal acquisition unit 111 acquires as the vibration signal the vibration corresponding to the tempo of music and representing the vibration in which the occurrence frequency of the vibration falls within the predetermined occurrence frequency range as the stimulus intensity range.

On the other hand, the occurrence frequency of vibration that is determined according to the tempo of the music being played can be used as an index that indicates the stimulus intensity given by the vibration. According to this embodiment, the occurrence frequency is adopted as such an index, and the stimulus intensity range is specifically set as the occurrence frequency range, so that vibration that obtains the desired arousal effect and/or the relaxing effect can be generated effectively.

Further, in this embodiment, the vibration signal acquisition unit 111 acquires the signal representing vibration corresponding to the frequency of the sound constituting the music code as the vibration signal.

According to this embodiment, generating vibration according to the frequency of the sound constituting the music code causes vibration for obtaining the arousal effect and/or the relaxing effect to be generated without impairing the taste of the music being played.

Further, in the present embodiment, the vibration signal acquisition unit 111 acquires as the vibration signal the signal representing the vibration in which the vibration amount of the vibration falls within the predetermined vibration amount range as the stimulus intensity range.

The vibration amount can be adopted as an index showing the stimulus intensity given by the vibration. According to this embodiment, the vibration amount is adopted as such an index, and the stimulus intensity range is specifically set as the vibration amount range, so that the vibration can be generated effectively that can obtain the desired arousal effect and/or the relaxing effect.

In this embodiment, two types of occurrence frequency range and vibration amount range are set as the stimulus intensity range. However, the stimulus intensity range referred to here may be only one of the occurrence frequency range and the vibration amount range, or a range in which some index indicating the intensity of the vibration stimulus other than the occurrence frequency and the vibration amount is used.

Further, the vibration control device 110 of this embodiment includes the first setting unit 114 that sets the stimulus intensity range in response to the user operation. Then, the vibration signal acquisition unit 111 acquires as the vibration signal the signal representing the vibration whose stimulus intensity falls within the stimulus intensity range set at the first setting unit 114.

According to this embodiment, the user can adjust the stimulus intensity range, that is, the stimulus intensity given by vibration to his/her desired intensity through the first setting unit 114. This makes it possible to effectively generate vibration that provides the desired arousal effect and/or relaxing effect for each user.

Further, the vibration control device 110 of this embodiment includes the biological information acquisition unit 115 and the second setting unit 116. The biological information acquisition unit 115 acquires the biological information representing the biological state of the user. The second setting unit 116 sets the stimulus intensity range based on the biological information acquired by the biological information acquisition unit 115. Then, the vibration signal acquisition unit 111 acquires as the vibration signal the signal representing the vibration whose stimulus intensity falls within the stimulus intensity range set at the second setting unit 116.

According to this embodiment, since the appropriate stimulus according to the biological condition is given to the user, it is possible to generate the vibration that appropriately obtains the desired arousal effect and/or the relaxing effect.

In this embodiment, the vibration control device 110 is illustrated that includes both the first setting unit 114 that sets the stimulus intensity range in response to the user operation and the second setting unit 116 that sets the stimulus intensity range based on biological information. However, the vibration control device is not limited to this, and may be one provided with only one of the first setting unit 114 and the second setting unit 116 described above.

Further, in this embodiment, as an example of a portion for setting the stimulus intensity range in response to the user's operation, the first setting unit 114 for adjusting the stimulus intensity to the intensity desired by the user is exemplified. However, the portion for setting the stimulus intensity range in response to the user's operation is not limited to this, and may be one that sets the stimulus intensity range selectively from a plurality of predetermined range candidates as in the second setting unit 116 described above.

Further, the vibration control device 110 of this embodiment includes the detection unit 117 and the generation unit 118. The detection unit 117 detects from the music the tempo of the music, the frequency of the sound constituting the code included in the music, and the strength of the sound as music elements. The generation unit 118 generates the vibration signal based on the music element detected by the detection unit 117. Then, the vibration signal acquisition unit 111 acquires the vibration signal generated by the generation unit 118.

According to this embodiment, generating the vibration signal based on the music element detected from the music being played causes the vibration for obtaining the arousal effect and/or the relaxing effect to be generated without impairing further the taste of the music being played.

Further, in the present embodiment, the second setting unit 116 sets the stimulus intensity range to be stronger when the biological information represents the drowsy state than when representing the arousal state, and to be weaker than when the biological information represents the excited state than when representing sedative state.

According to this embodiment, the drowsy user can effectively awaken, and the excited user can be effectively sedated and relaxed.

Further, the vibration control device 110 of the present embodiment includes the occurrence frequency range setting unit 116a that sets the occurrence frequency range for containing the occurrence frequency of vibration represented by the vibration signal based on the biological information. Then, the vibration signal acquisition unit 111 acquires as the vibration signal the signal that is vibration according to the tempo of music and whose occurrence frequency falls within the occurrence frequency range set by the occurrence frequency range setting unit 116a.

The occurrence frequency of vibration, which is determined according to the tempo of the music being played, can be used as an index indicating the stimulus intensity given by the vibration. According to this embodiment, the occurrence frequency is adopted as such an index, and the stimulus intensity range is specifically set as the occurrence frequency range, so that vibration that obtains the desired arousal effect and/or the relaxing effect can be effectively generated.

Further, in this embodiment, the vibration signal acquisition unit 111 acquires the signal representing vibration corresponding to the frequency of the sound constituting the music code as the vibration signal.

According to this embodiment, by generating the vibration according to the frequency of the sound constituting the music code, the vibration for obtaining the arousal effect and/or the relaxing effect can be generated without impairing the taste of the music being played.

Further, the vibration control device 110 of this embodiment includes the vibration amount range setting unit 116b that sets the vibration amount range for containing the vibration amount of the vibration represented by the vibration signal based on the biological information. Then, the vibration signal acquisition unit 111 acquires as the vibration signal the signal representing the vibration whose vibration amount falls within the vibration amount range set by the vibration amount range setting unit 116b.

The vibration amount can be adopted as the index representing the stimulus intensity given by the vibration. According to this embodiment, the vibration amount is adopted as such an index, and the stimulus intensity range is specifically set as the vibration amount range, so that the vibration that can obtain the desired arousal effect and/or the relaxing effect can be generated effectively.

Next, a second embodiment will be described.

Figure 3:
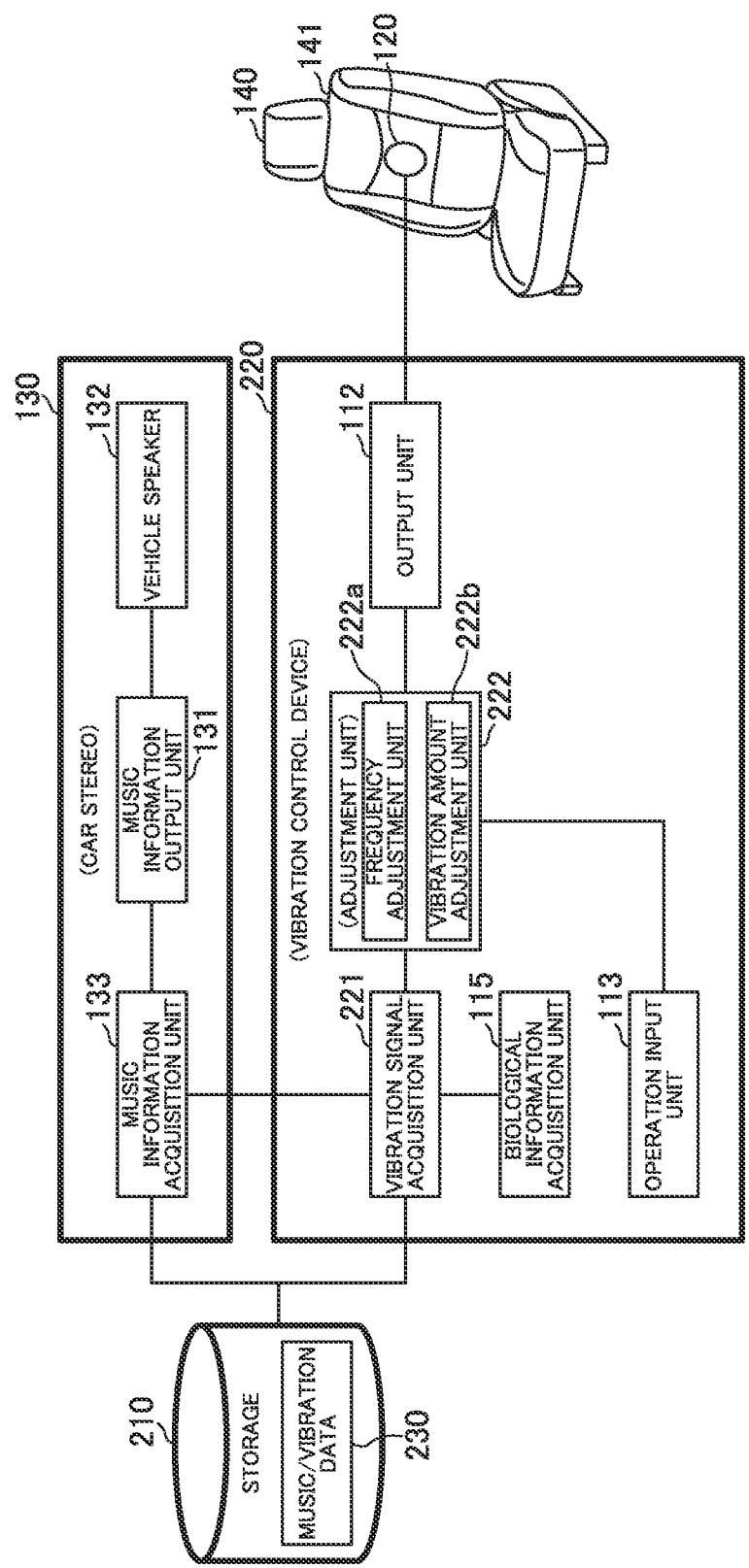
FIG. 3 is a schematic block diagram showing a vibration control device mounted on a moving body according to a second embodiment.

FIG. 3 is a schematic block diagram showing a vibration control device according to the second embodiment mounted on the moving body. In addition, in FIG. 3, components equivalent to the components of the first embodiment shown in FIG. 1 are designated by the same reference numerals as those in FIG. 1, and overlapping description of these equivalent components is omitted below.

Also in this embodiment, the moving body is a passenger car, and the same vibration device 120 and car stereo 130 as in the first embodiment are mounted, and the storage unit 210 and the vibration control device 220 are mounted. Note that FIG. 3 shows a music information acquisition unit 133, which is not shown in FIG. 1, for the car stereo 130. The music information acquisition unit 133 acquires music information from the storage unit 210. The music information output unit 131 outputs the music information acquired in this way to the vehicle speaker 132.

The storage unit 210 stores music/vibration correspondence data 230 used for control in the vibration control device 220 that controls the vibration device 120. The music/vibration correspondence data 230 has a data structure described below.

FIG. 4 is a schematic diagram showing data structure of the music/vibration correspondence data shown in FIG. 3 in a table format.

As shown in FIG. 4, the music/vibration correspondence data 230 includes a plurality of music information 231 representing music different from each other, and a signal set 232 associated with each of the plurality of music information 231. Each signal set 232 consists of three vibration signals, each representing a vibration in which the stimulus intensity falls within a predetermined stimulus intensity range. All of these three vibration signals represent vibrations corresponding to the music represented by the corresponding music information, and the stimulus intensity ranges are different from each other.

Each signal set 232 includes an arousal vibration signal, a normal vibration signal, and a relax vibration signal. The arousal vibration signal is a vibration signal corresponding to the stimulus intensity range that encourages the user to awaken. The normal vibration signal is a vibration signal corresponding to a normal stimulus intensity range that gives a moderate stimulus. The relax vibration signal is a vibration signal corresponding to a stimulus intensity range in which a weak stimulus is given to relax. In the example of FIG. 4, the music information M1 is associated with a signal set 232 including an arousal vibration signal S11, a normal vibration signal S12, and a relax vibration signal S13. Further, the music information M2 is associated with the signal set 232 including an arousal vibration signal S21, a normal vibration signal S22, and a relax vibration signal S23.

With such an association, the music/vibration correspondence data 230 is configured to control the vibration device 120 by the vibration signal associated with the music information 231 representing the music being played on the car stereo 130 among the plurality of music information 231.

Here, the frequencies of the arousal vibration signal, the normal vibration signal, and the relax vibration signal forming each signal set 232 are adjusted so that the vibration frequency represented by each vibration signal falls within a predetermined occurrence frequency range. As this frequency range, a frequency range of 20 Hz to 200 Hz is set as an example of a frequency range suitable for providing the arousal effect and/or the relaxing effect.

Further, the arousal vibration signal, the normal vibration signal, and the relax vibration signal all represent vibration according to the tempo of the music represented by the music information 231 associated with the signals, the frequency of the sound constituting the code included in the music, and the strength of the sound.

Further, also in this embodiment, the occurrence frequency range which is a range of vibration occurrence frequency and a vibration amount range which is a range of the vibration amount are adopted as the stimulus intensity range. In order to promote arousal, the arousal vibration signal represents the vibration in which the occurrence frequency falls within the arousal occurrence frequency range corresponding to a large occurrence frequency that gives a strong stimulus, and in which the vibration amount falls within the arousal occurrence frequency range corresponding to a large vibration amount that gives a strong stimulus. The normal vibration signal represents the vibration in which the occurrence frequency falls within the normal occurrence frequency range corresponding to the normal occurrence frequency that gives a moderate stimulus, and the vibration amount falls within the normal vibration amount range corresponding to the normal vibration amount that gives a medium stimulus. The relax vibration signal represents the vibration in which the occurrence frequency falls within the relax occurrence frequency range corresponding to a small occurrence frequency that gives a weak stimulus for relaxation and the vibration falls within the vibration amount falls within a relax vibration range corresponding to a small vibration amount that gives a weak stimulus.

The storage unit 210 for storing the music/vibration correspondence data 230 having such a data structure is mounted on the moving body and is a storage device of the computer on which the vibration control device 220 is constructed or a storage device installed externally on the computer. Further, the storage unit 210 is not limited to a storage medium mounted on the moving body and may be a known portable storage medium, or a storage medium or storage medium installed on a server connected to the computer via a network.

The vibration control device 220 shown in FIG. 3 acquires the vibration signal from such a storage unit 210, and uses the vibration signal to control the vibration device 120 installed on the back plate 141 of the seat 140. The vibration control device 220 includes a vibration signal acquisition unit 221 and an adjustment unit 222, in addition to the output unit 112, the operation input unit 113, and the biological information acquisition unit 115, which are the same as those in the first embodiment.

The vibration signal acquisition unit 221 in this embodiment acquires from the storage unit 210 a vibration signal of a signal set 232 associated with music information 231 acquired by the music information acquisition unit 133, which represents the music being played on the car stereo 130. At this time, in this embodiment, according to whether the user's biological state represented by the biological information acquired by the biological information acquisition unit 115 is a drowsy state, an arousal state, or an excited state, one vibration signal is acquired from the signal set 232. That is, the arousal vibration signal is acquired when the user's biological state is drowsy, the normal vibration signal is acquired when the user is in the arousal state, and the relax vibration signal is acquired when the user is in the excited state.

The adjustment unit 222, when receiving an adjustment operation from the user via the operation input unit 113, adjusts the vibration signal acquired by the vibration signal acquisition unit 221 for two points of the occurrence frequency and the vibration amount, which are the intensities of the vibration stimuli. The adjusting unit 222 includes a frequency adjusting unit 222a and a vibration amount adjusting unit 222b. The frequency adjusting unit 222a adjusts the vibration signal acquired by the vibration signal acquisition unit 221 so that the occurrence frequency increases or decreases by appropriately thinning or adding vibration generation timing according to the operation amount of the operation input unit 113. The vibration amount adjusting unit 222b adjusts the acquired vibration signal so that the vibration amount appropriately increases or decreases according to the operation amount of the operation input unit 113.

The adjusting unit 222 sends the vibration signal adjusted in this way to the output unit 112. Further, when there is no particular adjustment operation from the user, the adjustment unit 222 sends the vibration signal acquired by the vibration signal acquisition unit 221 to the output unit 112 as it is. Then, the output unit 112 outputs the vibration signal sent from the adjusting unit 222 to the vibration device 120 to generate vibration in the vibration device 120.

Figure 5:
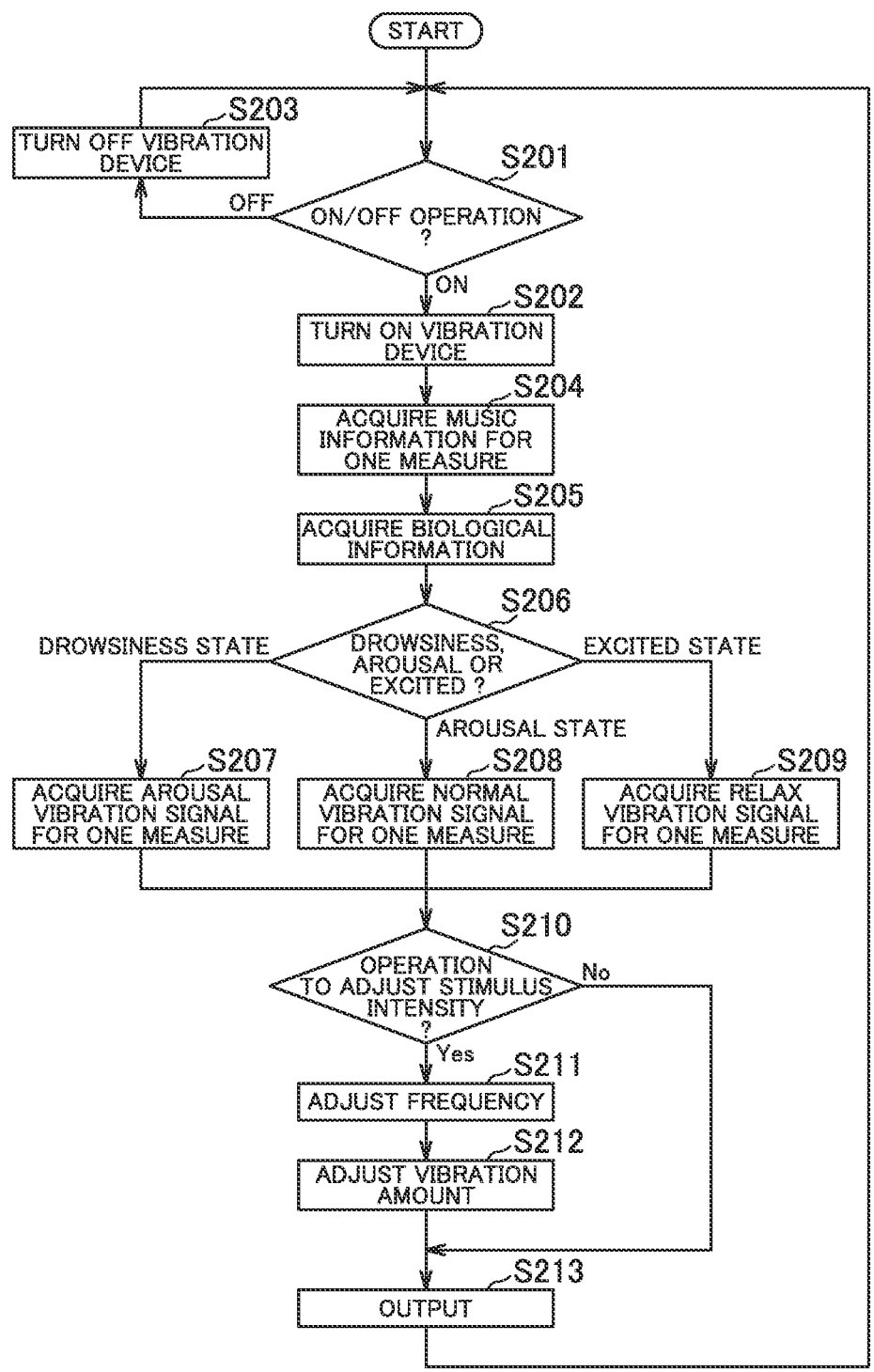
FIG. 5 is a flowchart showing a processing flow of a vibration control method executed by the vibration control device shown in FIG. 3.

FIG. 5 is a flowchart showing the processing flow of the vibration control method executed by the vibration control device shown in FIG. 3.

The process represented by this flowchart starts when the car stereo 130 starts playing music and the music information is sent to the vibration control device 220.

When the process starts, the adjustment unit 222 first determines whether or not the operation input unit 113 has been turned on/off for the power supply of the vibration device 120 after the music playback has started (step S201). When no particular operation is performed or when an on-operation is performed (on-determination of in step S201), the output unit 112 turns on if the power supply of the vibration device 120 is off at this point (step S202). In step S202, if the power of the vibration device 120 is on at this point, no particular process is performed and the process proceeds to the next step S204.

On the other hand, when the off-operation is performed (off-determination in step S201), the output unit 112 turns off if the power of the vibration device 120 turns on at this point (step S203), and returns to the process of step S201. In step S203, if the power supply of the vibration device 120 is off at this point, no particular process is performed and the process returns to step S201.

When the process proceeds to step S204 through step S202, in this step S204, the vibration signal acquisition unit 221 acquires the music information for one measure of the music being played from the music information acquisition unit 133 of the car stereo 130.

Subsequently, the biological information acquisition unit 115 acquires the biological information indicating whether the user's biological state is a drowsy state, a normal arousal state, or an excited state (step S205).

Next, the vibration signal acquisition unit 221 determines whether the biological state represented by the acquired biological information is the drowsy state, the arousal state, or the excited state (step S206).

When the biological state is drowsy (drowsiness determination in step S206), the vibration signal acquisition unit 221 reads and acquires the arousal vibration signal corresponding to the music information being played from the storage unit 210 for one measure (step S207).

When the biological state is the arousal state (arousal determination in step S206), the vibration signal acquisition unit 221 reads and acquires the normal vibration signal corresponding to the music information being played from the storage unit 210 for one measure (step S208).

When the biological state is the excited state (excitement determination in step S206), the vibration signal acquisition unit 221 reads and acquires the relax vibration signal corresponding to the music information being played from the storage unit 210 for one measure (step S209).

When the vibration signal is acquired in this way, the adjusting unit 222 then determines whether or not the stimulus intensity adjustment operation has been performed on the operation input unit 113 after music starts to playback (step S210).

When adjustment is operated (yes determination in step S210), the frequency tonality unit 222*a* of the adjustment unit 222 adjusts the occurrence frequency of vibration of the acquired vibration signal in increase/decrease according to the operation amount (step S211). Further, the frequency tonality unit 222*a* adjusts the vibration amount of the acquired vibration signal in increase/decrease according to the amount of operation (step S212).

If no adjustment is operated (no determination in step S210), these adjustment processes in the adjustment unit 222 are omitted.

The output unit 112 outputs the vibration signal adjusted or not adjusted by the adjustment unit 222 to the vibration device 120 (step S213). After that, the process returns to step S201 and the subsequent processes are repeated.

The processing of this flowchart is continued until the music is completed to playback on the car stereo 130.

In this embodiment, the vibration control program for executing the vibration control method shown in the flowchart in FIG. 5 by the computer is stored in a storage medium of some computer mounted on the moving body. Further, the storage medium for storing this vibration control program is not limited to the storage medium of some computer mounted on the mobile body, but may be a known portable storage medium or a storage medium installed in a server connected to this computer via a network.

According to the data structure of the music/vibration correspondence data 230 in the second embodiment described above, the storage medium or storage device as the storage unit 210, and the vibration control device 220 that controls using the music/vibration correspondence data 230, the following effects can be obtained.

According to this embodiment, it is possible to obtain the vibration signal representing the vibration in which the stimulus intensity falls within the predetermined stimulus intensity range while responding to the music being played, and to control the vibration device 120 by the vibration signal. Therefore, the vibration can be generated in the vibration device 120 in which such an effect can be obtained regardless of the contents of the music being played by performing the operation such as setting the stimulus intensity range to the desired range in which the desired arousal effect and/or the relaxing effect can be obtained. As described above, according to the present embodiment, it is possible to generate the vibration that can obtain the desired arousal effect and/or the relaxing effect regardless of the contents of the music while responding to the music being played.

Although the vibration device 120 and the vibration control device 220 mounted on the moving body are exemplified in this embodiment, the installation location of the vibration device 120 and the vibration control device 220 are not limited to the moving body. The vibration device 120 and the vibration control device 220 may be installed on a seat placed in a movie theater or a general residence as long as the user can be stimulated by vibration, and the installation location can be set arbitrarily.

Further, even when the vibration device 120 is mounted on the moving body, the installation position of the vibration device 120 is not limited to the back plate 141 of the seat 140 as in the present embodiment, and can be set arbitrarily as long as the user can be stimulated.

Here, in the data structure of the music/vibration correspondence data 230 in this embodiment, each of the plurality of music information 231*s* is associated with the signal set 232 composed of three vibration signals having different stimulus intensity ranges.

According to this embodiment, it is possible to perform the operation such as selecting the vibration signal in the stimulus intensity range suitable for arousal, relaxation, etc. from the signal set 232 associated with the music being played. This makes it possible to generate the vibration that provides the desired arousal and/or relaxing effect.

Further, in this embodiment, the vibration signal is a signal representing the vibration whose vibration frequency falls within the frequency range of 20 Hz to 200 Hz.

When the user is allowed to experience vibration as a stimulus, the frequency range of 20 Hz to 200 Hz can be mentioned as an example of the frequency range suitable for producing the arousal effect and/or the relaxing effect. According to this embodiment, the vibration frequency of the vibration represented by the vibration signal acquired by the vibration signal acquisition unit 221 is suppressed to such a frequency range, and the vibration is generated in which the arousal effect and/or the relaxing effect can be appropriately obtained.

Also in this embodiment, the frequency range containing the vibration frequency is not limited to the range of 20 Hz to 200 Hz, and is appropriately set as long as suitable for producing the arousal effect and/or the relaxing effect.

Further, in this embodiment, the vibration signal is the signal representing vibration according to the tempo of the music, the frequency of the sound constituting the code included in the music, and the strength of the sound.

According to this embodiment, the vibration of the vibration signal acquired by the vibration signal acquisition unit 221 corresponds to the tempo of the music being played and the frequency of the sounds constituting the code, so that the vibration generated by the vibration device 120 unlikely impairs the taste of the music being played. As described above, according to the present embodiment, the vibration for obtaining the arousal effect and/or the relaxing effect can be generated without impairing the taste of the music being played.

Also in this embodiment, as long as the vibration represented by the vibration signal is vibration corresponding to at least one of the tempo and the frequency of the sound constituting the code, the vibration may be based on only the tempo or the frequency of the sound constituting the code. In this case, the vibration element determined by the elements other than the tempo and the vibration element determined by the elements other than the frequency of the sound constituting the code are set according to some setting rule.

Further, in this embodiment, the vibration signal is the vibration corresponding to the tempo of music, and in which the occurrence frequency of the vibration represents the vibration contained within the predetermined occurrence frequency range as the stimulus intensity range.

On the other hand, the occurrence frequency of vibration that is determined according to the tempo of the music being played can be used as the index that indicates the stimulus intensity given by the vibration. According to this embodiment, the occurrence frequency is adopted as such an index, and the stimulus intensity range is specifically set as the occurrence frequency range, so that the vibration that obtains the desired arousal effect and/or relaxing effect can be effectively generated.

Further, in this embodiment, the vibration signal is a signal representing vibration according to the frequency of the sound constituting the music code.

According to this embodiment, by generating vibration according to the frequency of the sound constituting the music code, vibration for obtaining the arousal effect and/or the relaxing effect can be generated without impairing the taste of the music being played.

Further, in this embodiment, the vibration signal is the signal representing the vibration in which the vibration amount of the vibration falls within the predetermined vibration amount range as the stimulus intensity range.

The vibration amount can be adopted as the index showing the stimulus intensity given by the vibration. According to this embodiment, the vibration amount is adopted as such an index, and the stimulus intensity range is specifically set as the vibration amount range, so that the vibration that can obtain the desired arousal effect and/or the relaxing effect can effectively be generated.

Next, the third embodiment will be described.

Figure 6:
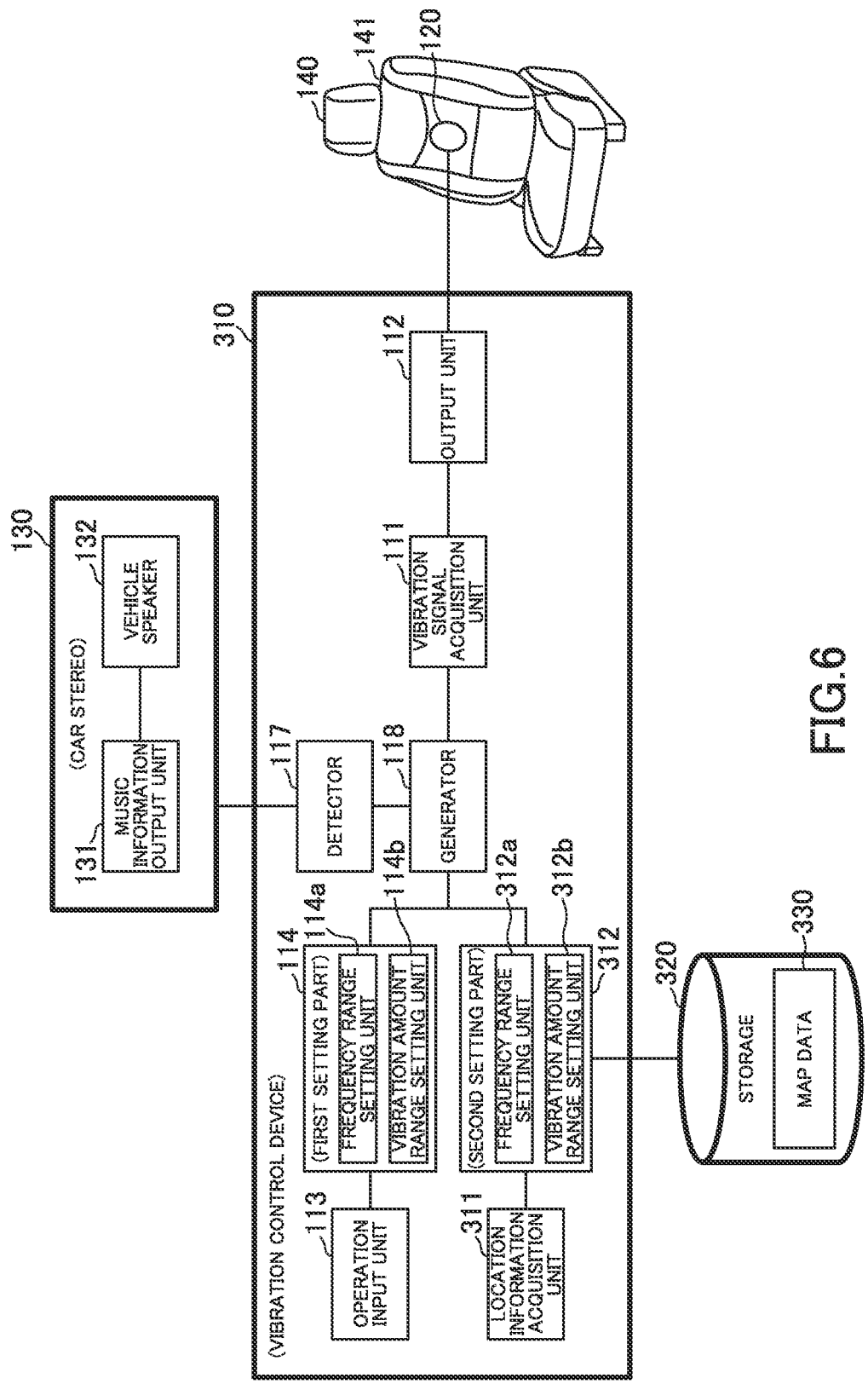
FIG. 6 is a schematic block diagram showing a vibration control device mounted on a moving body according to a third embodiment.

FIG. 6 is a schematic block diagram showing a vibration control device according to a third embodiment mounted on a moving body. Note that, in FIG. 6, components equivalent to the components of the first embodiment shown in FIG. 1 are designated by the same reference numerals as those in FIG. 1, and overlapping description of these equivalent components will be omitted in the following.

Also in this embodiment, the moving body is a passenger car, the same vibration device 120 and car stereo 130 as in the first embodiment are mounted, and a vibration control device 310 and a storage unit 320 are mounted.

A vibration control device 310 of this embodiment includes the same vibration signal acquisition unit 111, output unit 112, operation input unit 113, first setting unit 114, detection unit 117, and generation unit 118 as in the first embodiment. The vibration control device 310 includes a position information acquisition unit 311 and a second setting unit 312 as components that replace the biological information acquisition unit 115 and the second setting unit 116 in the first embodiment.

The position information acquisition unit 311 acquires a position of the moving body 1 using a positioning system such as GNSS (Global Navigation Satellite System). Further, in the present embodiment, the position information acquisition unit 311 identifies attributes of the road on which the moving body is located, such as a general road section and a highway section, based on this position, and generates and gets the position information representing the attribute of the road.

The second setting unit 312 sets an occurrence frequency range and a vibration amount range for containing an occurrence frequency and a vibration amount as an intensity of a vibration stimulus. In this embodiment, the second setting unit 312 compares settings of these ranges, the position represented by the position information acquired by the position information acquisition unit 311, with a map data 330 stored in the storage unit 320. The second setting unit 312 includes an occurrence frequency range setting unit 312*a* for setting the occurrence frequency range and a vibration amount range setting unit 312*b* for setting the vibration amount range.

FIG. 7 is a schematic diagram showing a data structure of the map data shown in FIG. 6 in a table format. Further, FIG. 8 is a schematic diagram showing the data structure shown in the table format in FIG. 7 in the map format.

As shown in FIGS. 7 and 8, a map data 330 includes a plurality of link information 331 each representing a road section, and an information set 332 associated with each of the plurality of link information 331. Each information set 332 consists of four pieces of information about the stimulus intensity. All of these four pieces of information are information representing the stimulus intensity range containing the intensity of the vibration stimulus.

Here, also in this embodiment, the occurrence frequency range, which is the range of the occurrence frequency of vibration, and the vibration amount range, which is the range of the vibration amount, are adopted as the stimulus intensity range. Further, in this embodiment, the occurrence frequency range and the vibration amount range are set for each of the two time zones, that is, for day and for night. For day when it is difficult for a mobile user to feel drowsy, the occurrence frequency range corresponding to a normal occurrence frequency that gives a moderate stimulus and the vibration amount range corresponding to a normal vibration amount are set. On the other hand, for night when the user tends to feel drowsy, in order to promote arousal, the occurrence frequency range corresponding to a large occurrence frequency that gives a strong stimulus and a vibration amount range corresponding to a large vibration amount that gives a strong stimulus are set.

Further, in FIGS. 7 and 8, as an example of a link information 331, a link information L11 whose attribute is a general road section and a link information L12 whose attribute is a highway section are exemplified. Further, a link information L13 of a start section of the autonomous driving correspondence road and a link information L14 of an end section of the autonomous driving correspondence road are also exemplified. The link information L11 of the general road section is associated with an information set 332 including information A111 and A112 of the occurrence frequency range for each day and night and information B111 and B112 of the vibration amount range for each day and night. The link information L12 of the highway section is associated with an information set 332 including information A121 and A122 of occurrence frequency range for each day and night and information B121 and B122 of vibration amount ranges for each day and night. The link information L13 of the start section of the autonomous driving correspondence road is associated with an information set 332 including information A131 and A132 of the occurrence frequency range for each day and night and information B131 and B132 for vibration amount ranges for each day and night. The link information L14 of the end section of the autonomous driving correspondence road is associated with an information set 332 including information A141 and A142 of occurrence frequency range for each day and night and information B1411 and B142 of vibration amount range for each day and night.

Here, in general, the user who drives the moving body is more likely to be drowsy when traveling on the highway section than when traveling on the general road section. Therefore, in this embodiment, the information A121, . . . , B122 corresponding to the link information L12 of the highway section is also information on stronger stimuli than the information A111, . . . , B112 corresponding to the link information L11 of the general road section.

Also, when driving on the autonomous driving correspondence road, it is possible for the user who drives the moving body to relax more than when traveling on other roads. On the other hand, at the end of the autonomous driving road, it is necessary to awaken from the relax state. Therefore, in the present embodiment, the information A131, . . . , B132 corresponding to the link information L13 of the start section for the autonomous driving correspondence road are all information on weaker stimuli than the information A141, . . . B142 corresponding to the link information L14 of the end section.

The map data 330 is configured so that the stimulus intensity can be set by the stimulus intensity information of the information set 332 associated with the link information 331 representing the road section in which the moving body is located. Further, since the stimulus intensity information of each information set 332 is set for each time zone for day and night, the stimulus intensity can be set for each time zone.

The storage unit 320 that stores the map data 330 having such a data structure is mounted on a moving body and is stored in a storage medium of a computer on which the vibration control device 310 is constructed, or a storage externally installed on the computer. Further, the storage unit 320 is not limited to the one mounted on a mobile body and fixedly installed, but may also be a known portable storage medium or a storage medium or storage installed in a server connected to the computer via a network. Further, in order to generate map data 330, the server connected to the vibration control device 310 via the network may acquire the position information, the time information, and the user's biological state of the moving body from a plurality of moving bodies, and specify the susceptibility to drowsiness for each road section with statistical processing, and set for each time zone the stimulus intensity information corresponding to each road section. The statistical processing executed by the server may be executed based on the information acquired from an unspecified number of mobiles, or may be executed individually for each mobile based on the information acquired from each mobile. The map data 330 generated in this way may be distributed to each moving body and stored in the storage unit 320 of the vibration control device 310.

The vibration control device 310 shown in FIG. 6 acquires the stimulus intensity information from such a storage unit 320, and controls the vibration device 120 installed on the back plate 141 of the seat 140 using the information.

In the vibration control device 310, as described above, the position information acquisition unit 311 acquires the information representing the attributes of the road on which the moving body is located as position information indicating the position of the moving body. Then, the occurrence frequency range setting unit 312a of the second setting unit 312 corresponds to the link information 331 representing the road section of the attribute represented by the acquired position information, and the occurrence frequency range information corresponding to the time zone at that time is obtained from the storage unit 320 and the occurrence frequency range is set. Similarly, the vibration amount range setting unit 312b corresponds to the link information 331 representing the road section of the attribute represented by the acquired position information, and obtains the information of the vibration amount range corresponding to the time zone at that time from the storage unit 320 and set the vibration amount range.

The generation unit 118 generates the vibration signal that represents vibration based on the tempo of the music being played, the frequency of the sound constituting the code, the strength of the sound, which are detected by the detection unit 117, the occurrence frequency range and the vibration amount range set by the second setting unit 312. The vibration represented by the vibration signal generated in this way corresponds to the music being played, and the occurrence frequency and the vibration amount fall within the occurrence frequency range and the vibration amount range set by the second setting unit 312, respectively. Then, the vibration signal acquisition unit 111 acquires the vibration signal generated by the generation unit 118, and the output unit 112 outputs the vibration signal to the vibration device 120 to generate vibration in the vibration device 120.

Figure 9:
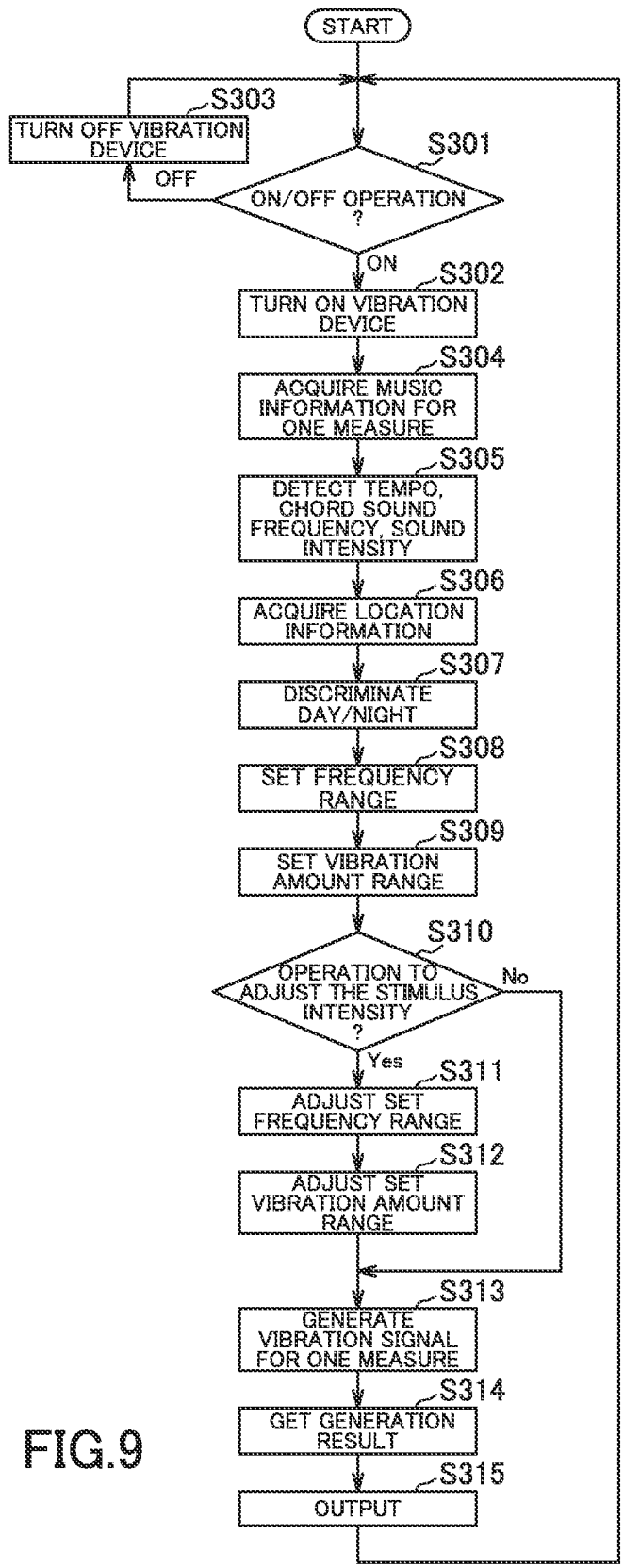
FIG. 9 is a flowchart showing a processing flow of the vibration control method executed by the vibration control device shown in FIG. 6.

FIG. 9 is a flowchart showing the processing flow of the vibration control method executed by the vibration control device shown in FIG. 6.

The process represented by this flowchart starts when the car stereo 130 starts playing music and the music information is sent to the vibration control device 310.

When the process starts, the generation unit 118 first determines whether or not the operation input unit 113 has been turned on/off for the power supply of the vibration device 120 after the music has started to playback (step S301). When no particular operation is performed or when an on-operation is performed (on-determination in step S301), the output unit 112 is turned on if the power supply of the vibration device 120 is off at this point (step S302). In step S302, if the power supply of the vibration device 120 is on at this point, no particular process is performed and the process proceeds to the next step S304.

On the other hand, when the off-operation is performed (off-determination in step S301), the output unit 112 is turned off if the power supply of the vibration device 120 is on at this point (step S303), and returns to the process of step S301. In step S303, if the power supply of the vibration device 120 is off at this point, no particular process is performed and the process returns to step S301.

When the process proceeds to step S304 through step S302, in this step S304, the detection unit 117 acquires the music information for one measure of the music being played from the music information output unit 131 of the car stereo 130. Subsequently, the detection unit 117 detects the tempo, the frequency of the sound constituting the code, and the strength of the sound based on the acquired music information (step S305).

Further, the position information acquisition unit 311 acquires the position information representing the attribute of the road on which the moving body is located (step S306). Further, the second setting unit 312 uses a timer (not shown) to determine whether the time zone at this time is day or night (step S307).

In the following step S308, an occurrence frequency range setting unit 312a corresponds to a link information 331 representing the road section of the attribute represented by the position information, and obtain from 320 information of the occurrence frequency range corresponding to any of the determined day and night zones and set the occurrence frequency range.

Further, in step S309, a vibration amount range setting unit 312b corresponds to the link information 331 representing the road section of the attribute represented by the position information, and obtain from the storage unit 320 the information of the vibration amount range corresponding to the determined time zone and set the vibration amount range.

When the occurrence frequency range and the vibration amount range are set in this way, the generation unit 118 next determines whether or not adjustment operation for the stimulus intensity has been performed on the operation input unit 113 after music starts to playback. (Step S310).

When an adjustment is operated (yes-determination in step S310), the occurrence frequency range setting unit 114a of the first setting unit 114 adjusts the set occurrence frequency range in increase/decrease according to the operation amount (step S311). Further, the vibration amount range setting unit 114b adjusts the set vibration amount range in increase/decrease according to the operation amount (step S312).

If no adjustment is operated (no-determination in step S310), step S311 and step S312 are omitted, and the process proceeds to the next step S313.

In step S313, the generation unit 118 generate the vibration signal corresponding to the music information for one measure based on the tempo obtained by the processing up to this point, the frequency of the sound constituting the code, the strength and weakness of the sound, the occurrence frequency range, and the vibration amount range. That is, the vibration signal representing the vibration is generated in which the occurrence frequency falls within the occurrence frequency range according to the tempo of the measure, the frequency falls within the frequency range of 20 Hz to 200 Hz while corresponding to the code of the measure, and the vibration amount falls within the vibration amount range while corresponding to the strength of the sound of the one measure.

The vibration signal acquisition unit 111 acquires the vibration signal for one measure generated in this manner (step S314), and the output unit 112 outputs the vibration signal to the vibration device 120 (step S315). After that, the process returns to step S301 and the subsequent processes are repeated.

The processing of this flowchart is continued until the music is completed to playback on the car stereo 130.

In this embodiment, a vibration control program for executing the vibration control method shown in the flowchart shown in FIG. 9 by a computer is stored in a storage medium of some computer mounted on the moving body. Further, the storage medium for storing this vibration control program is not limited to the storage medium of some computer mounted on the mobile body, but may be installed in a known portable storage medium or a storage medium installed on a server connected to this computer via a network.

According to the vibration control device 310, the vibration control method, the vibration control program, and the storage medium of the third embodiment described above, the following effects can be obtained.

There are roads, etc. on the road where the moving body moves, the road where the user who drives the moving body may easily feel drowsy, such as a highway, or conversely, the road where the moving body moves may be relax to some extent, such as an automatic driving correspondence road. According to this embodiment, the vibration signal representing the vibration corresponding to the position information indicating the position of the moving body while responding to the music being played is acquired and output to the vibration device 120. Therefore, the stimulus intensity given by the vibration can be set to an intensity suitable for the arousal effect and/or the relaxing effect according to the position of the moving body. Thereby, it is possible to generate the vibration that can obtain the desired arousal effect and/or the relaxing effect regardless of the contents of the music while being played.

Also in this embodiment, the installation position of the vibration device 120 in the moving body is not limited to the back plate 141 in the seat 140, and can be arbitrarily set as long as the user can be stimulated.

Here, in this embodiment, the position information acquisition unit 311 acquires the attributes such as a general road section and a highway section of the road on which the moving body is located as the position information.

According to this embodiment, the attributes of roads that affect the user's biological condition, such as expressways and autonomous driving correspondence roads, are acquired as the position information. Then, by generating vibration according to such position information, the arousal effect and/or the relaxing effect can be effectively obtained.

The position information acquired by the position information acquisition unit 311 is not limited to the information representing the attributes of the road as described above, and may be, for example, information representing the position itself of the moving body obtained by GNSS.

Further, the vibration control device 310 of this embodiment includes the second setting unit 312 that sets the stimulus intensity range containing the stimulus intensity based on the position information acquired by the position information acquisition unit 311. Then, the vibration signal acquisition unit 111 acquires the signal representing vibration whose stimulus intensity falls within the stimulus intensity range set by the second setting unit 312 as the vibration signal.

According to this embodiment, by setting the stimulus intensity range based on the position information, the user is given the appropriate stimulus according to the position of the moving body, so that the vibration can be generated in which the desired arousal effect and/or relaxing effect is appropriately obtained.

Further, in the present embodiment, the vibration signal acquisition unit 111 acquires the signal representing vibration whose vibration frequency falls within the frequency range of 20 Hz to 200 Hz as the vibration signal.

When the user is allowed to experience the vibration as the stimulus, the frequency range of 20 Hz to 200 Hz can be mentioned as an example of a frequency range suitable for producing an arousal effect and/or a relaxing effect. According to this embodiment, the vibration frequency of the vibration represented by the vibration signal acquired by the vibration signal acquisition unit is suppressed to such a frequency range to generate vibration in which the arousal effect and/or the relaxing effect can be appropriately obtained.

The frequency range for containing the vibration frequency is not limited to the range of 20 Hz to 200 Hz, and can be appropriately set as long as suitable for producing an arousal effect and/or a relaxing effect.

Further, in this embodiment, the vibration signal acquisition unit 111 acquires as the vibration signal the signal representing vibration according to the tempo of the music, the frequency of the sound constituting the code included in the music, and the strength of the sound.

According to this embodiment, the vibration of the vibration signal acquired by the vibration signal acquisition unit 111 corresponds to the tempo of the music being played and the frequency of the sounds constituting the code, so that the vibration generated by the vibration device 120 does not impair the taste of the music being played. As described above, according to the present embodiment, the vibration for obtaining the arousal effect and/or the relaxing effect can be generated without impairing the taste of the music being played.

The vibration represented by the vibration signal may be based only on the tempo or only the frequency of the sound constituting the code, as long as the vibration corresponds to at least one of the tempo and the frequency of the sound constituting the code. In this case, the vibration element determined by the elements other than the tempo and the vibration element determined by the frequency of the sound constituting the code are set according to some setting rule.

Further, in this embodiment, the occurrence frequency range setting unit 312*a* is provided to set the occurrence frequency range for containing the frequency of vibration represented by the vibration signal based on the position information acquired by the position information acquisition unit 311. Then, the vibration signal acquisition unit 111 acquires as the vibration signal the signal representing vibration that corresponds to the tempo of music and whose occurrence frequency falls within the occurrence frequency range set by the occurrence frequency range setting unit 312*a*.

The occurrence frequency of vibration, which is determined according to the tempo of the music being played, can be used as the index indicating the stimulus intensity given by the vibration. According to this embodiment, the occurrence frequency is adopted as such an index, and the stimulus intensity range is specifically set as the occurrence frequency range, so that the vibration that obtains the desired arousal effect and/or relaxing effect can effectively be generated.

Further, in this embodiment, the vibration signal acquisition unit 111 acquires the signal representing vibration corresponding to the frequency of the sound constituting the music code as the vibration signal.

According to this embodiment, by generating vibration according to the frequency of the sound constituting the music code, vibration for obtaining the arousal effect and/or the relaxing effect can be generated without impairing the taste of the music being played.

Further, the vibration control device 310 of the present embodiment has the vibration amount range setting unit 312*b* that sets the vibration amount range containing the vibration amount of the vibration represented by the vibration signal based on the position information acquired by the position information acquisition unit 311. Then, the vibration signal acquisition unit 111 acquires as the vibration signal the signal representing the vibration whose vibration amount falls within the vibration amount range set by the vibration amount range setting unit 312*b*.

The vibration amount of the vibration can be adopted as an index showing the stimulus intensity given by the vibration. According to this embodiment, the vibration amount is adopted as such an index, and the stimulus intensity range is specifically set as the vibration amount range, so that the vibration that can obtain the desired arousal effect and/or the relaxing effect can effectively be generated.

In this embodiment, two types of stimulus intensity ranges, the occurrence frequency range and the vibration amount range, are set. However, the stimulus intensity range referred to here may be only one of the occurrence frequency range and the vibration amount range, or may be a range using some index indicating the intensity of the vibration stimulus other than the occurrence frequency and the vibration amount.

Further, in this embodiment, vibration control device 310 is illustrated including both the first setting unit 114 that sets the stimulus intensity range in response to a user operation and the second setting unit 312 that sets the stimulus intensity range based on the position information. However, the vibration control device is not limited to this, and may be one provided with only one of the above-mentioned the first setting unit 114 and second setting unit 312.

Further, the vibration control device 310 of this embodiment includes the detection unit 117 and the generation unit 118. The detection unit 117 detects the tempo of the music, the frequency of the sound constituting the code included in the music, and the strength of the sound as music elements from the music. The generation unit 118 generates the vibration signal based on the music element detected by the detection unit 117. Then, the vibration signal acquisition unit 111 acquires the vibration signal generated by the generation unit 118.

According to this embodiment, by generating the vibration signal based on the music element detected from the music being played, the vibration for obtaining the arousal effect and/or the relaxing effect can be generated without further impairing the taste of the music being played.

Further, according to the data structure of the map data 330 shown in FIGS. 7 and 8 and the storage medium or storage device as the storage unit 320 in this embodiment, the following effects can be obtained.

According to the data structure of the map data 330 of this embodiment, the stimulus intensity information associated with the link information 331 representing the road section in which the moving body is located is obtained, and the vibration can be generated in the vibration device 120 in which the stimulus intensity is set based on the information. Therefore, the stimulus intensity given by the vibration can be set to the intensity suitable for the arousal effect and/or the relaxing effect according to the position of the moving body. As a result, it is possible to generate the vibration that can obtain the desired arousal effect and/or the relaxing effect regardless of the contents of the music while being played.

Here, in this embodiment, the stimulus intensity information associated with the link information L12 indicating the highway section has become the one stronger than the stimulus intensity information associated with the link information L11 indicating the general road section.

According to this embodiment, the appropriate arousal effect can be obtained by giving the strong stimulus to the user in the highway section where the user is more likely to get drowsy than the general road section.

Further, in this embodiment, the stimulus intensity information associated with the link information L13 indicating the start section of the autonomous driving correspondence road has become the one weaker than the stimulus intensity information associated with the link information L14 indicating the end section of the autonomous driving correspondence road.

According to this embodiment, in the start section of the autonomous driving correspondence road where relaxation is allowed, the appropriate relaxing effect can be obtained by softening the stimulus given to the user as compared with the end section.

Further, in this embodiment, the plurality of stimulus intensity information is associated with each of the plurality of link information 331 as information regarding the stimulus intensity for each time zone of day and night. The data structure of the map data 330 of this embodiment is configured so that the stimulus intensity can be set for each time zone by the plurality of stimulus intensity information associated with the link information 331 representing the road section in which the moving body is located.

In general, the user's biological condition may change according to the time zone, such as the user being more likely to feel drowsy at night than during the day. According to this embodiment, since the stimulus intensity can be set for each time zone, the vibration that obtains the appropriate arousal effect and/or relaxing effect according to the biological condition of the user for each time zone can be generated.

In this embodiment, two information for day and night on the occurrence frequency range and the information on the vibration amount range are set as information on the stimulus intensity. However, the setting of the information for each time zone referred to here is not limited to the setting of the two divisions of day and night, and may be set for each of a plurality of more subdivided time zones.

Further, in this embodiment, the stimulus intensity information is the information indicating the stimulus intensity range containing the stimulus intensity.

According to this embodiment, it is preferable to use the information indicating the stimulus intensity range because the stimulus intensity that changes every moment according to the music being played can be comprehensively set.

In this embodiment, two types of stimulus intensity ranges, the occurrence frequency range and the vibration amount range, are set. However, the stimulus intensity range referred to here may be only one of the occurrence frequency range and the vibration amount range, or may be a range using some index indicating the intensity of the vibration stimulus other than the occurrence frequency and the vibration amount.

Further, in this embodiment, as an example of the link information 331, the link information L11 of the general road section, the link information L12 of the highway section, the link information L13 of the start section of the autonomous driving correspondence road, and the link information L14 of the end section of the autonomous driving correspondence road are illustrated. However, the link information 331 is not limited to the information, and may be, for example, information indicating the range from the start point to the end point of the road section specified by GNSS.

Next, a modification of the map data 330 shown in FIGS. 7 and 8 with respect to the data structure in this embodiment will be described.

FIG. 10 is a schematic diagram showing the data structure of the modification example with respect to the data structure of the map data shown in FIGS. 7 and 8 in a table format. Further, FIG. 11 is a schematic diagram showing the data structure shown in the table format in FIG. 10 in a map format.

The map data 430 having the data structure shown in FIGS. 10 and 11 has a plurality of map element information 431 each representing an element on the map and an information set 432 associated with each of the plurality of map element information 431. Each information set consists of four pieces of information about the stimulus intensity. These four pieces of information, like four pieces of information contained in the information set 332 shown in FIGS. 7 and 8, serve as information representing the occurrence frequency range and the vibration amount range for each of the two time zones day and night.

In FIGS. 10 and 11, as an example of the map element information 431, information representing the first road link L21 corresponding to a general road and information representing a second road link L22 corresponding to a highway section are exemplified. Further, information representing a first node N23 corresponding to a branch point in the highway section and information representing a first area Ar24 including the autonomous driving correspondence road are exemplified.

The information representing the second road link L22 of the highway section is associated with the information set 432 of the occurrence frequency range or the vibration amount range corresponding to corresponding to the stimulus stronger than the occurrence frequency range and the vibration amount range of the information set 432 representing first road link L21 of the general road. Further, the information representing the first node N23 at the branch point is associated with the information set 432 of the occurrence frequency range and the vibration amount range corresponding to a stimulus stronger than the occurrence frequency range and vibration amount range of the information set 432 representing the second road link L22 of the highway section. Further, the information representing the first area Ar24 of the autonomous driving correspondence road is associated with the information set 432 of the occurrence frequency range and the vibration amount range corresponding to the stimulus weaker than the occurrence frequency range and the vibration amount of the information set 432 corresponding to the information representing the first road link L21 of the general road.

In FIGS. 10 and 11, the information of the first road link L21 in the general road section is associated with the information set 432 including the information A221 and A222 of the occurrence frequency range for each day and night and the information B221 and B222 of the vibration amount range for each day and night. The information of the second road link L22 of the highway section is associated with the information set 432 consisting of the occurrence frequency range information A221 and A222 for each day and night and the vibration amount range information B221 and B222 for each day and night. The information of the first node N23 at the branch point is associated with the information set 432 consisting of the occurrence frequency range information A231 and A232 for each day and night and the vibration amount range information B231 and B232 for day and night. The information representing the first area Ar24 of the autonomous driving correspondence road is associated with the information set 432 consisting of the information A241 and A242 for the occurrence frequency range for each day and night and the information B241 and B242 for each frequency amount range for each day and night.

The map data 430 having the data structure of the modified example described above is also configured so that the stimulus intensity can be set by the stimulus intensity information of the information set 432 associated with the map element information 431 corresponding to the position of the moving body. Further, the stimulus intensity information of each information set 432 is configured to set the stimulus intensity for each time zone since the stimulus intensity information is set for each time zone for day and night.

Similar to the map data 330 shown in FIG. 6, the map data 430 having such a data structure is stored on the storage medium of the computer mounted on the moving body on which the vibration control device 310 is installed, or the storage medium externally installed on the computer. Further, this storage unit is not limited to the one mounted on the mobile body and fixedly installed, but also may be a known portable storage medium or a storage medium or storage device installed in a server connected to the computer via a network. Further, in order to generate the map data 430, the server connected to the vibration control device 310 via the network may acquire from the plurality of moving bodies the position information, the time information, and the biological state of the user, and specify the susceptibility to drowsiness for each map element with statistical processing, and set the stimulus intensity information corresponding to each map element for each time zone. The statistical processing executed by the server may be executed based on the information acquired from an unspecified number of mobiles, or may be executed individually for each mobile based on the information acquired from each mobile. The map data 430 generated in this way may be distributed to each moving body and stored in the storage unit 320 of the vibration control device 310.

According to the data structure of the map data 430 of this modification, information on the occurrence frequency range and the vibration amount range associated with the map element information 431 representing the element to which the position of the moving body belongs is obtained, and the vibration in which the occurrence frequency and the vibration amount set based on that information can be generated in the vibration device 120. Therefore, the stimulus intensity given by the vibration can be set to the intensity suitable for the arousal effect and/or the relaxing effect according to the position of the moving body. As a result, it is possible to generate vibration that can obtain the desired arousal effect and/or the relaxing effect regardless of the contents of the music while being played.

Also in this modified example, two pieces of information on the occurrence frequency range and the vibration amount range are set for day and night as information on the stimulus intensity. However, the setting of the information for each time zone referred to here is not limited to the setting of the two divisions of day and night, and may be set for each of a plurality of more subdivided time zones.

Also, in this modified example, two types of ranges, the occurrence frequency range and the vibration amount range, are set as the stimulus intensity range. However, the stimulus intensity range referred to here may be only one of the occurrence frequency range and the vibration amount range, or may be a range using some index indicating the intensity of the vibration stimulus other than the occurrence frequency and the vibration amount.

The present invention is not limited to the examples and modifications described above, but includes other configurations that can achieve the object of the present invention, and the following modifications are also included in the present invention.

For example, in the above-mentioned first to third embodiments and modifications, the vibration control device 110, 220, and 310 on which the moving body as a passenger car is mounted are exemplified. However, the moving body on which the vibration control device is mounted is not limited to a passenger car, and may be a two-wheeled vehicle, a large vehicle such as a truck or a bus, or the like, and does not depend on the specific type of the moving body.

Further, in the first and third embodiments and modifications described above, the vibration signal acquisition unit 111 that acquires the vibration signal internally generated by the generation unit 118 of the vibration control device 110 and 310 mounted on the moving body is exemplified. Further, in the second embodiment described above, the vibration signal acquisition unit 221 that reads and acquires the vibration signal from the storage unit 210 mounted on the moving body is exemplified. However, the vibration signal acquisition unit is not limited to these, and may be, for example, one that acquires the vibration signal generated on a server outside the mobile body via a wireless network. Alternatively, the vibration signal may be read out and acquired from the storage unit built on the server via the wireless network.

REFERENCE SIGNS LIST

110, 220, 310 vibration control device
111,221 vibration signal acquisition unit
112 output section
113 operation input unit
114 first setting part
114a, 116a, 312a occurrence frequency range setting unit
114b, 116b, 312b vibration amount range setting unit
115 biological information acquisition department
116, 312 second setting part
117 detector
118 generator
120 vibration device
130 car stereo
131 music information output unit
132 vehicle speaker
133 music information acquisition department
140 sheet
141 back plate
210, 320 memory
222 adjustment department
222a frequency adjustment unit
222b vibration amount adjustment unit
230 music/vibration correspondence data
231, M1, M2 music information
232 signal set
311 location information acquisition unit
330 map data
331, L11, L12, L13, L14 link information
332,432 information set
431 map element information
A111, A121, A131, A141 information on the occurrence frequency range for day
A112, A122, A132, A142 information on the occurrence frequency range for night
B111, B121, B131, B141 information on the vibration amount range for day
B112, B122, B132, B142 information on vibration amount range for night
L21 first road link
L22 second road link
N23 first node
Ar24 first area
S11, S21 arousal vibration signal
S12, S22 normal vibration signal
S13, S23 relax vibration signal

What is claimed is:

1. A computer-implemented method for controlling a vibration device that generates vibration according to music being played so as to give a stimulus to a user, the method causing a computer to perform steps of:
receiving a music signal representing the music being played;
based on the music signal, generating a vibration signal that controls the vibration that is generated by the vibration device, the vibration signal representing the vibration in which an intensity of the stimulus falls within a predetermined stimulus intensity range; and
transmitting the vibration signal to the vibration device,
wherein the vibration signal corresponds to a tempo of the music, an occurrence frequency falling within a predetermined occurrence frequency range is determined according to the tempo, and the predetermined occurrence frequency range is set as the predetermined stimulus intensity range.

2. The method of claim 1, wherein the vibration signal generating step is executed so that the vibration signal corresponds to a frequency of a sound constituting code of the music.

3. The method of claim 2, wherein the vibration signal generating step is executed so that when a vibration amount of the vibration of the music falls within a predetermined vibration amount range, the predetermined vibration amount range is set as the predetermined stimulus intensity range.

4. The method of claim 1, wherein the vibration signal generating step is executed so that when a vibration amount of the vibration of the music falls within a predetermined vibration amount range, the predetermined vibration amount range is set as the predetermined stimulus intensity range.

5. The method of claim 1, further comprising:
setting the predetermined stimulus intensity range in response to an operation of the user, wherein the vibration signal generating step is executed so that the intensity of the stimulus falls within the predetermined stimulus intensity range.

6. The method of claim 1, further comprising:
acquiring biological information representing a biological state of the user; and
setting the predetermined stimulus intensity range based on the acquired biological information,
wherein the vibration signal generating step is executed so that the intensity of the stimulus falls within the predetermined stimulus intensity range set based on the acquired biological information.

7. The method of claim 1, further comprising:
detecting as a music element from the music at least one of the tempo of the music and a frequency of sound constituting code included in the music.

8. A non-transitory computer-readable storage medium on which is stored a vibration control program that, when executed by a computer, causes the computer to perform the method of claim 1.

* * * * *